US010898501B2

(12) United States Patent
Pace et al.

(10) Patent No.: US 10,898,501 B2
(45) Date of Patent: Jan. 26, 2021

(54) COMBINATION THERAPY EFFECTIVE AGAINST MICROORGANISMS, INCLUDING DRUG RESISTANT MICROORGANISMS

(71) Applicant: Fleurir ABX LLC, Raleigh, NC (US)

(72) Inventors: John Lee Pace, Burlington, NJ (US); Marc Edwin Wiles, Mason, OH (US); Stacy Michelle Adams, Cary, NC (US); Elizabeth Hussey, Chapel Hill, NC (US)

(73) Assignee: FLEURIR ABX, LLC, Raleigh, NC (US)

( * ) Notice: Subject to any disclaimer, the term of this patent is extended or adjusted under 35 U.S.C. 154(b) by 140 days.

(21) Appl. No.: 15/527,705

(22) PCT Filed: Nov. 18, 2015

(86) PCT No.: PCT/US2015/061324
§ 371 (c)(1),
(2) Date: May 17, 2017

(87) PCT Pub. No.: WO2016/081592
PCT Pub. Date: May 26, 2016

(65) Prior Publication Data
US 2018/0369259 A1 Dec. 27, 2018

Related U.S. Application Data

(60) Provisional application No. 62/245,095, filed on Oct. 22, 2015, provisional application No. 62/104,805, (Continued)

(51) Int. Cl.
*A61K 31/665* (2006.01)
*A61K 45/06* (2006.01)
(Continued)

(52) U.S. Cl.
CPC .......... *A61K 31/665* (2013.01); *A61K 31/505* (2013.01); *A61K 31/635* (2013.01);
(Continued)

(58) Field of Classification Search
CPC .... A61K 31/665; A61K 45/06; A61K 31/505; A61K 31/635
See application file for complete search history.

(56) References Cited

FOREIGN PATENT DOCUMENTS

| CN | 101790683 A | 7/2010 |
| TW | 201632177 | 9/2016 |

OTHER PUBLICATIONS

EPO Form 1224, EPO Communication, Supplementary European Search Report for EP Application No. 15860075.9, dated Jul. 10, 2018 (1 page).
(Continued)

*Primary Examiner* — San Ming R Hui
(74) *Attorney, Agent, or Firm* — Monique A. Vander Molen

(57) ABSTRACT

Novel antimicrobial compositions comprise at least a form of a fosfomycin (or suitable analogs, or derivatives thereof), and at least one sulfonamide (or suitable analogs, or derivatives thereof), and/or at least one diaminopyridine (or suitable analogs, or derivatives thereof). Said antimicrobial compositions generally include two or more of said components as a novel combination, provided in a single combination or formulation, or provided independently with overlapping exposures of the two or more components. These novel compositions, when provided as the two or more components, are effective against susceptible microorganisms, and are effective against susceptible drug-resistant microorganisms (e.g., bacteria, parasites), including multi-drug resistant bacteria. These novel compositions are also effective against microorganisms or strains thereof now
(Continued)

susceptible to the combination even though said microorganisms or strains thereof were previously found or were considered resistant or intolerant to at least one of the components of the novel composition, when the at least one component was used alone at what was considered an effective dosing amount or concentration.

21 Claims, 5 Drawing Sheets

Related U.S. Application Data filed on Jan. 18, 2015, provisional application No. 62/081,394, filed on Nov. 18, 2014.

(51) Int. Cl.
A61K 31/505 (2006.01)
A61K 31/635 (2006.01)
A61P 31/04 (2006.01)

(52) U.S. Cl.
CPC .............. *A61K 45/06* (2013.01); *A61P 31/04* (2018.01); *A61K 2300/00* (2013.01); *Y02A 50/473* (2018.01); *Y02A 50/478* (2018.01)

(56) References Cited

OTHER PUBLICATIONS

EPO Form 1507S, EPO Communication, extended Supplementary European Search Report for EP Application No. 15860075.9, dated Jul. 10, 2018 (9 pages).
International Preliminary Report on Patentability and Written Opinion for the International Searching Authority for PCT/US2015/061324 dated May 23, 2017, pp. 1-8.
Rodriguez, A, et al. "Synergic activity of fosfomycin in association with other antibacterial agents: A review," Drugs Exptl Clin Res, 1980, vol. 6, No. 4, pp. 281-288.
Morshed, MG, et al., "Evaluation of agents for use in medium for selective isolation of lyme disease and relapsing dever *Borrelia* species," European J Clin Microbiol Infect Diseases, 1993, vol. 12, No. 7, pp. 512-518.
Van Duin, A, "Suppression of urinary tract infections with fosfomycin and trimethoprim-sulfamethoxazole: A case report," J. Chemotherapy, 2011, vol. 23, No. 1, pp. 55-56.
Blomer, RH, et al., "Tinea capitis profunda durch *Trichophyton verrucosum* mit abszedierender superinfection durch cMRSA bei einem kleinkind," Kasuistiken, Der Hautarzt, 2012, vol. 63, pp. 648-652.
English translation of abstract for Blomer, RH, et al., as "Tinea capitis profunda due to *Trichophyton verrucosum* with cMRSA superinfection in an infant," 2012, 5 pp., available at https://link.springer.com/articles/10.1007%2Fs00105-012-2326-y.
Leelarasamee, A, et al., "In vitro activity of fosfomycin, alone and in combination with trimethoprim/sulfamethoxazole against blood isolates of methicillin-susceptible and methicillin-resistant *Staphylococcus aureus*," Interscience Conference on Antimicrobial Agents and Chemotherapy, Poster session Sep. 11, 2012, Abstract #E-1477, 1 page.
Schweitzer, BI, et al., "Dihydrofolate reductase as a therapeutic target," The FASEB Journal, 1990, vol. 4, pp. 2441-2452.
Docobo-Perez, F, et al., "Pharmacodynamics of fosfomycin: Insights into clinical use for antimicrobial resistance," Antimicrobial Agents Chemother, 2015, vol. 59, No. 9, pp. 5602-5610.
Tang H., et al., "A novel model for prediction of human drug clearance by allometric scaling," Drug Metabolism Disposition, 2005, vol. 33, No. 9, pp. 1297-1303.
Lefort A, et al., "Activity of fosfomycin alone or combined with cefoxitin in vitro and in vivo in a murine model of urinary tract infection due to *Escherichia coli* harbouring CTX-M-15-type extended-spectrum beta-lactamase," Int J Antimicrobial Agents, 2014, vol. 43, pp. 366-369.
US Department of Health and Human Services, et al., "Guidance for industry, estimating the maximum safe starting dose in the initial clinical trials for therapeutics in adult healthy volunteers," Jul. 2005, pp. 1-30.
Hutabarat, R, et al. "Disposition of drugs in cystic fibrosis. I. Sulfamethoxazole and trimethoprim," Clin Pharmacol Therapeutics, 1991, vol. 49, No. 4, pp. 402-409.
Cornell University, et al., "CARE625.01 Treating mice for infection with sulfamethoxazole and trimethoprim in drinking water," Standard Operating Procedure, Oct. 2005, pp. 1-2.
Office Action for Taiwan Application No. 104138153, dated Dec. 12, 2019, received electronically in Jan. 2020, 6 pages.
Translation of Office Action for Taiwan Application No. 104138153, dated Dec. 12, 2019, received electronically in Jan. 2020, 6 pages.
Translation of Office Search Report for Taiwan Application No. 104138153, dated Oct. 14, 2019, received electronically in Jan. 2020, 1 page.
Borowski, J., et al., "Combined action of fosfomycin with beta-lactam and aminoglycoside antibiotics," Chemotherapy 1977, vol. 23(Suppl. 1):82-85.
Daza, R., et al., "Interactions of fosfomycin with other antibiotics," Chemotherapy 1977, vol. 23(Suppl. 1):86-92.
Gevaudan, M.J.., et al., "Recherche de synergie entre la fosfomycine et divers autres antibiotiques," Med. Maladies Infect. 1978, vol. 8(12):657-665.
Gialdroni Grassi, G., et al., "Attivita antibatterica della fosfomicina," Giornale Italiano di Chemioterapia, 1976, vol. 23(2):87-94.
Martin, I., et al., "Estudios de sinergismo entre fosfonomicina y otros antibioticos," Antibioticos y Quimioterapicos. 1971, vol. 1(2):113-118.
Miksza-Zylkiewicz, R., et al., "Combined action of phosphomycin with streptomycin and gentamycin," Archivum Immunologiae et Therapiae Experimentalis. 1977, vol. 25(6):741-747.
Moreno-Lopez, M., et al., "Phosphonomycin (MK-955). Quantitative sensitivity spectra of various hospital strains to this new antibiotic," Microbiologia Espanola, 1971, vol. 24:79-85.
Olay, T., et al., "Interaction of fosfomycin with other antimicrobial agents: in vitro and in vivo studies," J. Antimicrobial Chemotherapy 1978, vol. 4(6):569-576.
Perea, E.J., et al., "Synergism of fosfomycin-ampicillin and fosfomycin-chloramphenicol against *Salmonella* and *Shigella*," Antimicrobial Agents Chemotherapy 1978, vol. 13(5):705-709.
Rodriquez, A., "Estudios sobre interaccion 'in vitro' de fosfomicina con eritromicina," Farmaes 1978, vol. 142:87-97.
Ullmann, U., "Synergism between fosfomycin and nalidixic acid in vitro," J. Antimicrobial Chemotherapy 1979, vol. 5(5):612-613.

PRIOR ART

COMBINATION THERAPY EFFECTIVE AGAINST MICROORGANISMS, INCLUDING DRUG RESISTANT MICROORGANISMS

CROSS REFERENCE TO RELATED APPLICATIONS

A portion of the disclosure of this patent document contains material which is subject to copyright work protection. The copyright work owner has no objection to the facsimile reproduction by anyone of the patent document or the patent disclosure, as it appears in the Patent and Trademark Office patent file or records, but otherwise reserves all copyright rights whatsoever. This application claims the benefit of priority to U.S. Provisional Patent Application Number 62/081,394, filed on Nov. 18, 2014, and to U.S. Provisional Patent Application Number 62/104,805, filed on Jan. 18, 2015, and to U.S. Provisional Patent Application Number 62/245,095, filed on Oct. 22, 2015, all of which are hereby incorporated by reference in their entirety, and to the maximum extent allowable by law.

FIELD OF THE INVENTION

The subject application describes novel compositions provided as pharmaceutical compositions comprising a combination having unexpectedly high synergistic activity against microorganisms, including both Gram negative and Gram positive bacteria, and drug resistant strains of bacteria, as well as parasites. Unpredictably, said compositions are also effective against bacteria and/or parasites that are resistant to one or more compounds contained in the combination.

BACKGROUND

Resistance of a microorganism to a pharmaceutical antibiotic typically leads to a decline in efficacy of said antibiotic. It also, as expected, leads to a decline in use of said antibiotic against the resistant microorganisms. Some antibiotics for which resistant strains have developed remain in use against mild to moderate infections. Said antibiotics are not often acceptable or effective for use against severe infections, or hospital-acquired infections, including infections to which one or more antibiotics are resistant.

There remains a need for effective compositions, and therapies that have activity not only against microorganisms that cause or contribute to mild to moderate infections, but are also effective, and provide sustained activity, and effectiveness, against microorganisms that cause or contribute to severe infections, including infections developed by resistant strains of Gram negative or Gram positive bacteria, or developed from or contributed by parasites. These and other needs are met by the compositions described below.

SUMMARY

Described herein are novel compositions and uses for said novel compositions. Said compositions overcome one or more of the above described problems or obstacles. For example, the described novel compositions effectively kill microorganisms, including bacteria, and/or inhibit growth of said microorganisms, including bacteria, and/or drug-resistant bacteria, and/or multi-drug resistant bacteria, and/or parasites, and/or drug-resistant parasites.

The novel compositions have broad spectrum activity, including activity against both Gram-positive bacteria (e.g., Staphylococci, Enterococci, Streptococci, Clostridia) and Gram-negative bacteria (e.g., *E. coli*, *H. influenzae*, and other Enterobacteriaceae, *Pseudomonas aeruginosa*, *Proteus mirabilis*, and *Neisseria gonorrhoeae*). The broad spectrum activity includes activity against drug-resistant bacteria. The bacteria may be a multi-drug resistant bacteria, or a pan-resistant bacteria. The activity may include parasites. The microorganisms (e.g., bacteria and/or parasites) are those susceptible to one or more of the components of the compositions described herein.

Said compositions include a combination of compounds or agents. In some embodiments, when said composition (that includes the combination of compounds or agents) is provided to one or more susceptible microorganisms or to a subject indicated to contain or containing the one or more susceptible microorganisms, the combination of compounds or agents exhibit activity or a therapeutic effect with regard to the one or more susceptible microorganisms.

In some embodiments, when said composition (that includes the combination of compounds or agents) is provided to one or more susceptible microorganisms or to a subject indicated to contain or containing the one or more susceptible microorganisms, the combination of compounds or agents exhibit a synergistic effect with regard to the one or more susceptible microorganisms. The synergistic effect is considered an activity or therapeutic effect that is greater than the activity or therapeutic effect of said agents or compounds when used separately. As such, when provided as a combination of compounds or agents at least one of the compounds or agents in the combination, or more than one of the compounds or agents in the combination, may be provided at the same doses or at doses lower than used currently and/or effectively for each compound when provided separately. The same or lower doses for the combination described herein includes effective doses that are the same or are often lower than the current indications or recommendations for use of at least one of the independent compounds or agents utilized in the described combination. In some embodiments, when the composition described herein (the described combination of compounds or agents) is provided to one or more susceptible microorganisms or to a subject indicated to contain or containing the one or more susceptible microorganisms, the combination of compounds or agents described herein exhibit activity or a therapeutic effect with regard to the one or more susceptible microorganisms, at said doses that are the same or are lower based on current indications or recommendations for use of each independent compound or agent when used alone.

The compositions described herein and containing a combination of compounds may be provided to the one or more susceptible microorganisms, or to a subject indicated to contain or containing the one or more susceptible microorganisms, such that the composition is provided as the combination of compounds. The components of the combination (e.g., the compounds or agents) may be provided independently, provided sequentially, or provided concomitantly. Providing concomitantly may include providing together, such as in a blend, mixture, or in a same dose or formulation. Providing concomitantly may include providing simultaneously, or concurrently, or providing in parallel, such as at or about a same time or at or about a same schedule. In some embodiments, at least part of a daily dosing or administration schedule of the more than one compound or agent in the composition may overlap. On a same day, the more than one compound or agent of the combination may be provided independently and/or together.

In one or more embodiments, a composition described herein includes a combination of two or more compounds or agents described herein, in which one of said compounds or agents is a combination of two independent compounds or components. Activity, and/or efficacy of such a composition may be comparable in activity, and/or efficacy with at least one of said agents or compounds when said one agent or compound is used separately. Activity, and/or efficacy of such a composition as described herein may be comparable in activity, and/or efficacy or provide better activity, and/or efficacy than the activity or therapeutic effect of each of the compounds or agent used alone, or when used in a manner currently prescribed for use of said independent compounds or agents (utilized as prescribed, and not in the combinations described herein).

In one or more embodiments, a composition described herein includes a combination of two or more compounds or agents described herein, in which one of said compounds or agents is a specific combination of two independent compounds or components, such that the activity, and/or efficacy of the composition (which is the combination of the two or more compounds or agents, in which one of said agents is the specific combination of two independent compounds or components) is not only greater than the activity or therapeutic effect of one of said agents or compounds when used separately, but is also greater than the activity or therapeutic effect of the specific combination of the two independent compounds or components as they may be prescribed for use as the specific combination.

In one or more embodiments, said compositions (comprising two or more compounds or agents) have unexpectedly been found to exhibit activity, and/or are effective against bacterial strains that are resistant to at least one of the two or more compounds or agents when the two or more compounds were tested separately. In one or more embodiments, said compositions (comprising two or more compounds or agents) have unexpectedly been found to exhibit activity, and/or are effective against bacterial strains that are resistant to each of the two or more compounds or agents when the two or more compounds were tested separately. In one or more embodiments, said compositions (comprising two or more compounds or agents) have unexpectedly been found to exhibit, activity and/or are effective against bacterial strains that are resistant to the specific combination of the two of the independent compounds or components typically used in combination. Heretofore, bacteria exhibiting resistance to a compound or agent, or to the specific combination of the two independent compounds or components typically used in the specific combination, have not been found to later be susceptible to said compound or agent, or to said specific combination of the two independent compounds or components used in the specific combination. Unexpectedly, however, when compositions are so combined as described herein, bacterial strains that were resistant to the separate compound or agent (and/or to the specific combination of the two independent compounds or components) are now susceptible to the novel compositions described herein that includes the specific combination of the two or more compounds or components.

In some embodiments, activity, and/or efficacy of the described novel compositions may be found to be better or far better than a four-fold reduction in the minimal inhibitory concentration (MIC) typically used to define synergy when assessed by a checkerboard microdilution assay. When the compositions described herein are provided to one or more target microorganisms having a diminished response to an alternative compound (e.g., exhibiting reduced susceptibility or exhibiting resistance to the alternative compound), the activity, and efficacy may be far better than would be expected with a simple additive response. In some embodiments, efficacy of the compositions described herein are far superior than expected, based on the efficacy of the two or more compounds or agents when used separately on the same microorganisms (e.g., same type of microorganisms).

In some embodiments, efficacy of the compositions described herein (which may include a first compound or agent, and a second compound or agent, the second compound including the specific combination of two independent components) are better or far better than when the first compound or agent or the second compound are used independently on the same microorganisms (e.g., same type of microorganisms). In some embodiments, the activity, and/or efficacy of the described compositions are far greater than would be predicted based on the activity, and/or efficacy of each individual compound on susceptible microorganisms. In some embodiments, the first compound is a first component or agent, and the second compound is a second component or agent. In some embodiments, the first compound is a first component or agent, and the second compound is a combination of two independent components or agents.

Unexpectedly, and in some embodiments, the novel compositions described herein exhibit synergistic growth inhibition as well as bactericidal synergy ($\geq 3$ $\log_{10}$ change in viable count assessed by a minimal bactericidal concentration and time-kill assay after 24 hours, as compared with the compounds or agents used separately).

In additional embodiments are compositions (comprising the two or more compounds or agents), and methods of use including methods for inhibiting or preventing growth of one or more microorganisms that were previously not considered susceptible to the two or more compounds or agents when used separately or as they are independently indicated for use.

Also described herein are compositions, and methods of use of said compositions, including methods for stopping further microbial growth, including methods for killing microbial cells. Methods may be performed in vivo, ex vivo, in vitro, in situ etc. Methods described herein may be for killing or inhibiting further growth of one or more microorganism, including one or more drug resistant microorganisms, such as an antibiotic-resistant microorganism.

Still further are pharmaceutical compositions, and methods for treating an organism (multi-cellular) or mammal in need thereof, such as a mammal exhibiting susceptibility to or an infection from or considered to be due to one or more microorganisms. In some embodiments, said infection may be considered a severe infection. In some embodiments, said infection may include an infection requiring hospitalization. In some embodiments, said microorganisms may be one or more resistant strains of microorganisms, such as those considered antibiotic resistant. In some embodiments, methods described herein include treating at least one resistant strain of microorganism by administering, to a subject susceptible to, and/or exhibiting a possible infection or a known infection from the at least one resistant strain of the microorganism, a therapeutic dose of a composition described herein, one comprising a combination of two or more compounds or agents, each of the of two or more compounds or agents considered an antimicrobial agent on its own that could be provided to the patient independently. In some embodiments, the patient may have previously been found to be resistant to or less susceptible to one or all of the two or more compounds or agents when used independently on the patient. In one or more embodiments, treating includes administering to a subject in need. Treatment may occur in an office, or a home, as suitable examples. In some embodiments, the treatment may be in a hospital, the subject having or exhibiting a serious or severe infection.

In some embodiments, pharmaceutical compositions, and methods are described herein for treating a drug-resistant microbial infection (e.g., an antibiotic-resistant microbial infection). The method comprises administering a therapeutic dose of a composition described herein, one comprising a combination of two or more compounds or agents, each of the of two or more compounds or agents considered an antimicrobial agent on its own.

Methods, and composition described herein may be particularly useful for treating infections that arose from one or more drug-resistant microorganisms.

The described compositions may also serve as compositions for sterilization, and/or to prevent contamination by one or more microorganisms, including microorganisms that may exhibit resistance to an antimicrobial. Methods for sterilization, and/or for preventing contamination include applying the described composition to the surface in need of sterilization or decontamination. The surface may be organic or inorganic, living or non-living, moveable or non-moveable, including surfaces at a facility, or on a structure, device, and/or equipment.

In some embodiments, any of the novel compositions may be further combined with another anti-infective agent or composition, such as another antibacterial agent or composition, or with an antiviral agent or composition, or with an antifungal agent or composition, or with an anti-parasitic agent or composition.

The novel compositions described herein may be provided in therapeutically acceptable doses for the treatment of one or more susceptible infections, including but not limited to respiratory tract, and/or lung infections, systemic infections, gastrointestinal infections, skin infections, and genitourinary tract infections.

The novel compositions described herein may be provided in therapeutically acceptable doses for the treatment of one or more susceptible infections, including but not limited to respiratory tract, and/or lung infections, systemic infections, gastrointestinal infections, skin infections, and genitourinary tract infections found resistant to one or more alternative antimicrobial drugs.

The novel compositions described herein may be provided in therapeutically acceptable doses for the treatment of one or more susceptible infections, including but not limited to respiratory tract, and/or lung infections, systemic infections, gastrointestinal infections, skin infections, and genitourinary tract infections found resistant to one or more of the components in the composition described herein (e.g., when said component was used alone at its therapeutically acceptable dose for treatment of said one or more infections).

The novel compositions described herein may also be provided in concentrated doses, in which one or all of said components of the novel compositions require at least one dilution prior to providing the novel composition for the treatment of one or more susceptible infections, including but not limited to respiratory tract, and/or lung infections, systemic infections, gastrointestinal infections, skin infections, and genitourinary tract infections.

The novel compositions described herein will be useful, such as in therapeutically acceptable doses, against at least one or more of the following microorganisms: *Staphylococcus* spp. (e.g., methicillin-resistant *Staphylococcus aureus* (MRSA)), *Streptococcus* spp., *Enterococcus* spp., *Bacillus anthracis*, Enterobacteriaceae (e.g., *Escherichia coli, Klebsiella pneumoniae*, and *Enterobacter cloacae*), *Pseudomonas aeruginosa, Stenotrophomonas maltophila, Burkholderia* spp., *Acinetobacter baumanii, Proteus mirabilis, Proteus vulgaris, Providencia* sp., *Morganella morganii, Haemophilus influenzae, Moraxella catarrhalis, Legionella pneumophila,* and *Yersinia pestis*. Compositions described herein are also active against additional microorganisms, including but not limited to biowarfare agents, and bacterial strains resistant to other antibacterial classes including, for example, extended spectrum beta-lactamase, carbaepenemase producing *E. coli*, and *K. pneumoniae*, carbapenem-resistant, multidrug- or pan-resistant *P. aeruginosa*. Said novel compositions may be used effectively in humans and in animals.

Novel compositions may comprise a therapeutically effective amount of the composition provided as an antimicrobial.

The novel compositions will include a combination of compounds or agents comprising at least a fosfomycin, or a suitable salt, analog, derivative, or prodrug thereof, any of which have inhibitory activity in cell wall (peptidoglycan) synthesis (e.g., inhibit MurA or cell wall synthesis). The combination may further comprise one or more sulfonamide, including analogs, and derivatives thereof, any of which have inhibitory activity in the metabolism of folic acid. Additionally or alternatively, the combination may further comprise one or more diaminopyridine, including analogs, and derivatives thereof, any of which have inhibitory activity in the metabolism of folic acid. The combination of described components may be provided in a form described herein for the treatment of one or more infections described above. The combination of described components may be provided in a form described herein for use with a microorganism susceptible to the novel composition. The combination of described components may be provided in a form described herein for use with a susceptible microorganism, in which a low MIC is found within the "susceptible" range. The combination of described components may be provided in a form described herein for the treatment of one or more bacterial infections. The combination of described components may be provided in a form described herein for the treatment of one or more complicated bacterial infections. The described novel compositions may further comprise an excipient. The one or more sulfonamide and the one or more diaminopyridine may be provided as a combination. Said combination of the sulfonamide to diaminopyridine may be in a ratio of between about 3:1 and about 6:1. Additional ranges may also be acceptable. Said combination of the sulfonamide to diaminopyridine may be in a ratio of between about 3:1 and about 19:1 (e.g., for Cmax).

The described novel compositions may be administered to a subject in need thereof. The described novel compositions may be administered in addition to one or more of another agent selected from the group consisting of antibiotic, antiviral agent, antifungal agent, anti-parasitic agent, and combinations thereof. Each described novel composition is effective at killing or inhibiting growth of a bacteria and/or parasite or other microorganism considered to be involved or responsible for the one or more infections described above. The bacteria may be a Gram positive bacteria involved or responsible for the one or more infections described above. The bacteria may be a Gram negative bacteria involved or responsible for the one or more infections described above. The bacteria may be any one or more of a group of Gram positive bacteria. The bacteria may be any one or more of a group of Gram negative bacteria. The bacteria may be a combination of one or more Gram positive bacteria and one or more Gram negative bacteria. Representative bacteria include but are not limited to *Staphylococcus* spp., including methicillin-resistant *Staphylococcus aureus*, *Streptococcus* spp., *Enterococcus* spp., *Bacillus anthracis*, Enterobacteriaceae, including *Escherichia coli*, *Klebsiella pneumoniae*, and *Enterobacter cloacae*, *Pseudomonas aeruginosa*, *Stenotrophomonas maltophila*, *Burkholderia* spp., *Acinetobacter baumanii*, *Proteus mirabilis*, *Proteus vulgaris*, *Providencia* sp., and *Morganella morganii*, *Haemophilus influenzae*, *Moraxella catarrhalis*, *Legionella pneumophila*, and *Yersinia pestis*.

In additional embodiments are pharmaceutical compositions suitable for killing a microorganism in a subject in need thereof, the composition comprising a fosfomycin, and one or more of at least one sulfonamide, and/or at least one diaminopyridine. The pharmaceutical compositions may be provided for treatment of one or more bacterial infection or parasitic infection, including but not limited to those described above. The pharmaceutical compositions may be provided for prevention of one or more bacterial infection or parasitic infection. The pharmaceutical compositions may be provided for prevention or treatment of one or more complicated infections. The fosfomycin may include a pharmaceutically acceptable salt, ester or prodrug, including analogs, and derivatives thereof. Components of the pharmaceutical composition may be in separable forms, or a premix form, or some combination thereof.

In additional embodiments are antimicrobial pharmaceutical compositions suitable for parenteral injection comprising two or more of a fosfomycin, a sulfamethoxazole; and a trimethoprim. The combination of agents may be provided for the treatment of one or more bacterial infections described above. The combination of agents may be provided for the treatment of one or more complicated bacterial infections. The fosfomycin may include a pharmaceutically acceptable salt, ester or prodrug, including an analog, and derivative thereof. Components of the antimicrobial pharmaceutical composition may be in separable forms or a premix form or some combination thereof.

In further embodiments are antimicrobial pharmaceutical compositions suitable for oral administration comprising two or more of a fosfomycin, a sulfamethoxazole; and a trimethoprim. The combination of agents may be provided for the treatment of one or more infections described above. The combination of agents may be provided for the treatment of one or more uncomplicated infections. The combination of agents may be provided for the treatment of one or more complicated infections. The fosfomycin may include a pharmaceutically acceptable salt, ester or prodrug, including an analog, and derivative thereof. Components of the antimicrobial pharmaceutical composition may be in separable forms or a premix form or some combination thereof.

In further embodiments are antimicrobial pharmaceutical compositions suitable for inhalation comprising two or more of a fosfomycin, a sulfamethoxazole, and a trimethoprim. The combination of agents may be provided for the treatment of one or more infections described above. The combination of agents may be provided for the treatment of one or more uncomplicated infections. The combination of agents may be provided for the treatment of one or more complicated infections. The fosfomycin may include a pharmaceutically acceptable salt, ester or prodrug, including an analog, and derivative thereof. Components of the antimicrobial pharmaceutical composition may be in separable forms or a premix form or some combination thereof.

The above described antimicrobial pharmaceutical compositions may be active against at least one of the group consisting of complicated urinary tract infections, complicated respiratory tract infections, including lung infections associated with cystic fibrosis, hospital acquired bacterial pneumonia, acute exacerbation of bronchitis associated with chronic obstructive pulmonary disease, ceftriaxone resistant infections, and drug-resistant abdominal infections.

With the compositions described herein are methods of inhibiting growth, or of killing a microorganism, including a Gram-positive bacteria, a Gram-negative bacteria, a parasite, a drug-resistant bacteria, and/or a drug-resistant parasite. One representative method comprises providing a therapeutically effective amount of a composition described herein to the microorganism, the composition comprising a combination of agents, the combination of agents comprising at least a fosfomycin, and one or more of at least one sulfonamide, and/or one or more of at least one diaminopyridine, said combination inhibiting growth of the microorganism, or killing the microorganism. The therapeutically effective amount of the composition described herein may increase the area under the concentration curve (AUC) of at least one of the fosfomycin, the sulfonamide, and the diaminopyridine, upon administration, as compared with an individual administration of any one of the fosfomycin, the sulfonamide, and the diaminopyridine when administered alone. The fosfomycin may include a pharmaceutically acceptable salt, ester or prodrug, or an analog, or derivative thereof, any of which have inhibitory activity in cell wall biosynthesis (e.g., inhibit peptidoglycan synthesis, MurA synthesis). The at least one sulfonamide may include an analog, or derivative thereof, any of which have inhibitory activity in the synthesis of folic acid, or is sulfamethoxazole. The at least one diaminopyridine may include an analog, or derivative thereof, any of which inhibit dihydrofolate reductase, or is trimethoprim, or is pyrimethamine. The microorganism may be a bacteria. The microorganism may be a parasite. The microorganism may be one suspected of causing a bacterial infection and/or parasitic infection, such as described above, or selected from one or more in the group including, but not limited, to gastrointestinal infection, genitourinary infection, respiratory infection, a skin infection, a systemic infection, a wound infection, a sexually transmitted infection, or sexually transmitted infection disease. The microorganism may be resistant to one or more antibacterial agents. The microorganism may be resistant to one or more anti-parasitic agents. The microorganism may be resistant to one or more of the fosfomycin, the sulfonamide, and the diaminopyridine. The microorganism may reside in a subject. The subject may be any of a human, and an animal and has a condition associated with or indicating an infection from the microorganism. The infection may be mild, moderate or severe. The infection may be a gastrointestinal infection, urogenital infection, respiratory infection, a skin infection, a systemic infection, a wound infection, and/or a sexually transmitted disease. The microorganism may reside in a subject and the composition described herein is provided to the subject by an administrative route. The compositions described herein may be provided by a means of oral administration, parenteral administration, topical administration, ocular administration, intramuscular administration, transdermal administration, and/or nasal administration. Known means of said administrations are well known in the art.

In even further embodiments are methods of treating an infection, such as a bacterial infection, or a parasitic infection, in a subject in need thereof. One representative method includes administering to a subject suspected of having the infection a therapeutically effective composition as described herein, in which the composition comprises a combination of agents comprising at least a fosfomycin, and one or more of a sulfonamide, and/or a diaminopyridine. The composition may also comprise a combination comprising at least a fosfomycin, a sulfonamide, and a diaminopyridine. The therapeutically effective amount of the composition may increase the AUC of at least one of the fosfomycin, the sulfonamide, and the diaminopyridine upon administration as compared with an individual administration of any one of the fosfomycin, the sulfonamide, and the diaminopyridine when administered alone. The AUC may be the AUC/MIC or the f AUC/MIC (free drug AUC above the MIC), because the MIC is decreased for the combinations described herein. Even when current doses of each of the components are used in combinations described herein (doses based on current indicated doses of each individual component when used individually), AUC in relation to the MIC is different in the combinations described herein. In some of the combinations described herein, AUC in relation to MIC will drive efficacy of the novel combinations described herein. For example, AUC in relation to MIC should drive efficacy of the fosfomycin component in the combinations described herein. The fosfomycin may include a pharmaceutically acceptable salt, ester or prodrug, including an analog, or derivative thereof. The sulfonamide may be sulfamethoxazole, or one or more sulfonamides. The diaminopyridine may be one or more diaminopyridines. The diaminopyridine may be trimethoprim. The diaminopyridine may be pyrimethamine. The diaminopyridine may be trimethoprim and pyrimethamine, or similar or suitable combination. The infection may be selected from the group consisting of a gastrointestinal infection, urogenital infection, respiratory infection, a skin infection, a systemic infection, a wound infection, and a sexually transmitted disease. The infection may be resistant to one or more of the fosfomycin, the sulfonamide, and the diaminopyridine. The bacterial infection may be resistant to one or more antibacterial agents. The bacterial infection may be resistant to one or more of the fosfomycin, the sulfonamide, and the diaminopyridine. The bacterial infection may be resistant to one or more of the fosfomycin, the sulfonamide, and the diaminopyridine. The parasitic infection may be resistant to one or more anti-parasitic agents. The sulfonamide to diaminopyridine, when both are included, may be in a ratio between about 3:1 and 6:1. The fosfomycin, the sulfonamide, and the diaminopyridine may be provided by administering in any one of the groups consisting of independently, sequentially, simultaneously, concomitantly, and combinations thereof. The subject may be any of a human, and an animal. The administering may be by any route selected from the group consisting of oral, parenteral, topical, ocular, intramuscular, transdermal, nasal, and combinations thereof.

With the description herein, novel antimicrobial compositions are provided, said compositions comprising at least a form of a fosfomycin or an analog, or derivative thereof, and a sulfonamide (or an analog, or derivative thereof), and/or a diaminopyridine (or an analog, or derivative thereof). Said antimicrobial compositions may and generally include two or more of said components. Some or all of said components may be provided as a combination, such as a single combination, or some or all of said components may be provided independently yet provided in a schedule or daily regimen for suitable, and/or maximal efficacy, and/or reduced dosing frequency, and/or reduced dosing amount. The dosing frequency and/or dosing amount of the two or more components will include a dosing of at least one of the components that is less than the dosing frequency and/or dosing amount when said one component is used alone. In one or more embodiments, the dosing frequency and/or dosing amount of the two or more components will include a dosing of each of the components in a dosing frequency and/or dosing amount that is considered safe, based at least in part on the safety of each of the two or more components when used alone. Said schedule, and the dosing frequency of the components, may be based on pharmacokinetic, and pharmacodynamic analysis. A representative example of such parameters is provided below.

The novel antimicrobial compositions described herein are found effective against susceptible microorganisms. The novel antimicrobial compositions when provided in an effective schedule and dosing frequency will be found effective against a broad spectrum of bacteria and/or parasites, which may include drug-resistant bacteria, multi-drug resistant bacteria, and/or drug-resistant parasites. Said drug-resistant bacteria and/or parasites may, in some embodiments, also be resistant to one, some, or all of the components of the novel antimicrobial composition described herein (e.g., one or more of the form of the fosfomycin, the sulfonamide, and/or the diaminopyridine, or when the sulfonamide, and the diaminopyridine, are provided as a combination).

In some embodiments, the antimicrobial pharmaceutical composition described herein comprises at least a therapeutically effective amount a fosfomycin; and a therapeutically effective amount at least one sulfonamide, such that the composition inhibits growth of a microorganism, or kills the microorganism, the microorganism suspected of causing an infection, such as a complicated bacterial infection, or a parasitic infection, the fosfomycin provided as a pharmaceutically acceptable salt, ester, or prodrug, or an analog or derivative thereof, any of which have inhibitory activity in cell wall or peptidoglycan synthesis of the microorganism (e.g., acting on MurA), and the antimicrobial pharmaceutical composition being in a separable form, or a premix form. The sulfonamide may be provided as a pharmaceutically acceptable salt, ester, or prodrug, or an analog or derivative thereof. The therapeutically effective amount of at least one of the fosfomycin, and the sulfonamide, may be less than an amount indicated as a therapeutically effective amount when used alone. The sulfonamide may be provided as sulfamethoxazole. The microorganism may be a microorganism resistant to the fosfomycin, and/or the sulfonamide.

In some embodiments, the antimicrobial pharmaceutical composition described herein comprises at least a therapeutically effective amount a fosfomycin; and a therapeutically effective amount at least one diaminopyridine, such that the composition inhibits growth of a microorganism, or kills the microorganism, the microorganism suspected of causing an infection, such as a complicated bacterial infection, or a parasitic infection, the fosfomycin provided as a pharmaceutically acceptable salt, ester or prodrug, or an analog or derivative thereof, any of which have inhibitory activity in cell wall synthesis of the microorganism, and the antimicrobial pharmaceutical composition being in a separable form or a premix form. The therapeutically effective amount of at least one of the fosfomycin, and the diaminopyridine, may be less than an amount indicated as a therapeutically effective amount when used alone. The diaminopyridine may be provided as a pharmaceutically acceptable salt, ester, or prodrug, or an analog or derivative thereof. The diaminopyridine may be provided as trimethoprim. The diaminopyridine may be provided as pyrimethamine. The diaminopyridine may be provided as a combination of at least two diaminopyridines. The diaminopyridine may be provided as a combination of trimethoprim and pyrimethamine, as an example, providing activity as a broad spectrum antimicrobial agent, as an antibacterial agent and an anti-parasitic agent.

In any of the described compositions, the composition may further comprise a carrier to increase the AUC of the composition or of at least one of the components of the composition. The carrier may increase said AUC upon administration, as compared with a composition without the carrier. In any of the described compositions, the composition may have an increased AUC/MIC (because of lower MIC with the synergistic combination) upon administration, as compared with at least one of the fosfomycin, the sulfonamide, or the diaminopyridine, when said fosfomycin, sulfonamide, or diaminopyridine is used alone. In any of the compositions described herein, a therapeutically effective amount of the composition includes an amount of at least one of the components that is less than an amount of that component indicated as a therapeutically effective amount when used alone, such as for treatment of a bacterial infection for which one or more is indicated for use.

These and additional embodiments are further described below.

BRIEF DESCRIPTION OF THE DRAWINGS

For a more complete understanding of the description provided herein, and the advantages thereof, reference is now made to the brief description below, taken in connection with the accompanying drawing and detailed description.

DETAILED DESCRIPTION

Figure 1:
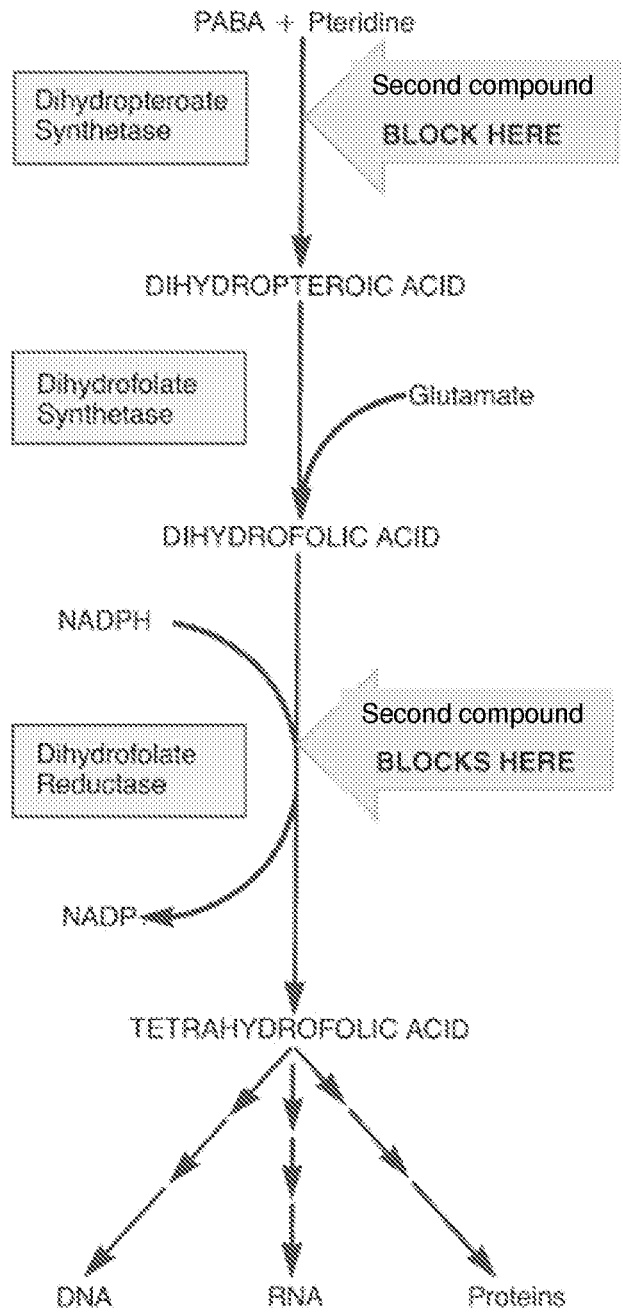
FIG. 1 illustrates a representative, and known metabolic pathway.

Although making and using various embodiments are discussed in detail below, it should be appreciated that as described herein are provided many inventive concepts that may be embodied in a wide variety of contexts. Embodiments discussed herein are merely representative, and do not limit the scope of the invention.

The novel compositions described herein includes a combination of compounds or agents. Individually, each compound or agent on its own may provide only mild or moderate antimicrobial activity, and/or effectiveness. In combination, the grouping of said compounds or agents in the unique arrangements, and formulations described herein unexpectedly allow said compounds to behave synergistically. Surprisingly, the synergistic effect is greater than predicted.

The combination of the described composition includes at least a first compound or agent. The first compound or agent is or includes a form of a fosfomycin. In one or more forms, the fosfomycin has a structure as represented by formula I, or formula II, in which formula II is a fosfomycin salt depicted as a disodium salt, or formula III, which is a monobasic hydrosoluble fosfomycin salt depicted as fosfomycin tromethamine (fosfomycin-trometamol). The fosfomycin includes any of said formulas, suitable analogues, derivatives, salts, esters, or prodrugs thereof. The salts may include, chemically, (−)(cis-1,2-epoxy-propyl)phosphonic acid. Said salts may include mono-salts, and di-salts (e.g., sodium, potassium, calcium, magnesium), as well as salts formed with amines, such as α-phenethylamine, quinine, lysine, procaine, etc., which can be mono- or di-salts. The first compound or agent may also comprise any analogues, and derivatives, and salts thereof of the representative compounds as described, and illustrated but not limited to those of formula I, II, and III.

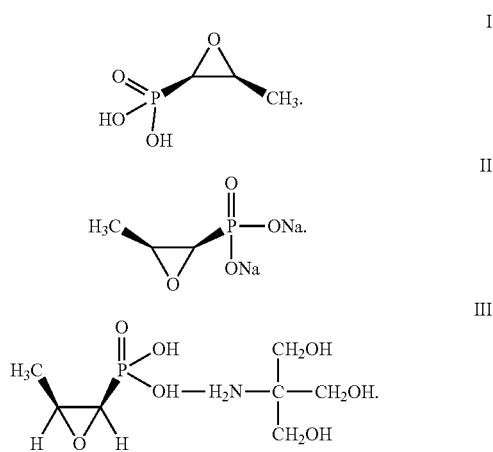

In some embodiments, a fosfomycin calcium salt form may be more suitable, such as when other salts are not suitable, or are too large. The first compound or agent may include analogues, and/or derivatives thereof having inhibitory activity of cell wall synthesis (inhibits MurA or peptidoglycan synthesis).

The first compound or agent has activity against Gram-positive bacteria, and Gram-negative bacteria, and may be therapeutically useful in the treatment of infections caused thereby. These bacteria will include but are not limited to Staphylococcus aureus, Klebsiella spp., Streptococcus pyogenes, Enterobacter spp., Streptococcus pneumoniae, Serratia marcescens, Enterococcus faecalis, Pseudomonas aeruginosa, Neisseria meningitidis, Salmonella spp., Neisseria gonorrhoeae, Shigella spp., Haemophilus influenzae, Campylobacter jejuni, Legionella pneumophila, Yersinia enterocolitica, Escherichia coli, Acinetobacter calcoaceticus, Acinetobacter baumanii, Indole (−) Proteus spp., Vibrio cholerae, Indole (+) Proteus spp., Aeromonas spp., Peptococcus spp., Fusobacterium spp., Peptostreptococcus spp., and Clostridium spp. The first compound or agent in some forms has a history of use, such as being provided orally, and by IV, for use with urinary tract infections, and respiratory tract infections, said use providing a long safety record, as is available to one of ordinary skill in this field.

A second compound of the described compositions may be or may include a sulfonamide or at least one sulfonamide having a functional group represented in formula IV.

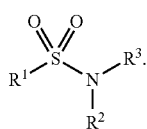

IV

The sulfonamide may also include a $N^1$-heterocyclic substituted sulfonamide, such as a 5- or 6-membered heterocycle (e.g. a pyrimidine, pyrazine, pyridazine, oxazole, isoxazole, thiazole or thiadiazole ring). Specific examples include but are not limited to sulfadiazine, sulfamethoxazole, sulfatroxazole, sulfamerazine, sulfadoxine, sulfadimethoxine, sulfamethazine, sulfapyrazole, sulfaquinoxaline, sulfachloropyridazine, sulfaguanidine, sulfalene, sulfametin, sulfamethoxine, sulfamethoxy-pyridazine, sulfamethylphenazole, sulfaphenazole, sulfamoxole, sulfapyrazine, sulfapyridazine, sulfapyridine, sulfasymazine, sulfathiozole, sulfametrole, and sulfixoazole. The second compound may include analogues, derivatives, and/or prodrugs thereof having inhibitory activity in the synthesis of dihydrofolate, as depicted in FIG. 1 (see, e.g., top arrow "Second compound Block Here").

In one or more embodiments, the sulfonamide may be represented by sulfamethoxazole (SMX) represented by formula V, or may be its analogue, derivative, prodrug, salt, or thereof.

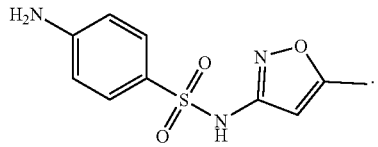

V

The second compound or agent in the described compositions may also include or may further comprise or may be replaced by at least one diaminopyridine, including those analogues, derivatives, and/or prodrugs that inhibit dihydrofolate reductase, as also depicted in FIG. 1 (bottom arrow "Second compound Blocks Here"). An example includes pyrimethamine. Another example includes 2,4-diaminopyrimidine, and analogues, and derivatives thereof, such as 2,4-diamino-5-benzyl-pyrimidines. Further examples include but are not limited to 2,4-diamino-5-(4-amino-3,5-dichlorobenzyl)pyrimidine, 2,4-diamino-5-(3,5-dichloro-4-methylaminobenzyl)pyrimidine, 2,4-diamino-5-(3,5-dichloro-4-ethylaminobenzyl)pyrimidine, 2,4-diamino-5-(3,5-dichloro-4-dimethylaminobenzyl)pyrimidine, 4-diamino-5-(4-acetamido-3,5-dichlorobenzyl)pyrimidine. They may also include diaminopyridine with substitutions in the phenyl ring such as 2,4-diamino-5-(3,4,5-trimethoxybenzyl)-pyrimidine (trimethoprim), 2,4-diamino-5-[3,5-dimethoxy-4-(2-methoxyethoxy)benzyl]-pyrimidine (tetroxoprim), and 2,4-diamino-5-(3,5-dimethoxy-4-methylthiobenzyl)-pyrimidine (metioprim). Other dihydrofolate reductase inhibitors include 2,4-diamino-5-(4-bromo-3,5-dimethoxybenzyl)-pyrimidine, 2,4-diamino-5-[3,5-diethoxy-4-pyrrol-1-yl)-benzyl]-pyrimidine, 2,4-diamino-5-(3,4-dimethoxybenzyl)-pyrimidine (diaveridine), 2,4-diamino-5-(p-chlorophenyl)-6-ethylpyrimidine (pyrimethamine), 2,4-diamino-5-(2-methyl-4,5-dimethoxybenzyl)-pyrimidine; (RS)-5-[(2-cyclopropyl-7,8-dimethoxy-2H-chromen-5-yl)methyl]pyrimidine-2,4-diamine (iclaprim), and 5-[(4-bromo-3,5-dimethoxyphenyl)methyl]pyrimidine-2,4-diamine (brodimoprim), as further non-limiting examples.

In one or more embodiments, the diaminopyridine may be represented by a formula VI, which is pyrimethamine, or may be any analogue, derivative, prodrug, salt, or ester thereof.

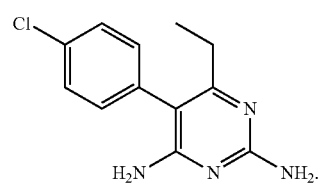

VI

In one or more embodiments, the diaminopyridine may be represented by a formula VII, which is trimethoprim (TMP), or may be any analogue, derivative, prodrug, salt, or ester thereof.

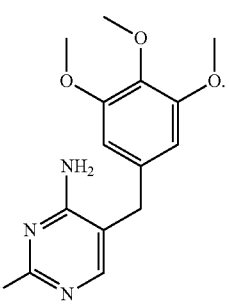

VII

The second compound may be one or more of a sulfonamide (SM), and/or a diaminopyridine (DP) having inhibitory activity in the dihydrofolate pathway (as described above).

Interestingly, resistance to the first compound or agent, the fosfomycin (a phosphonic acid derivative, cis-1,2-epoxypropyl phosphonic acid, also provided as a monobasic hydrosoluble fosfomycin salt, or fosfomycin-trometamol) has occurred, sometimes frequently, in many clinically relevant bacteria (both Gram negative, and Gram positive). As an anti-infective, it is only approved for use in the U.S. in a salt form as fosfomycin tromethamine (((1R,2S)-(1,2-epoxypropyl)phosphonic acid, and 2-amino-2-(hydroxymethyl)-1,3-propanediol (1:1)) for treatment of mild (uncomplicated) urinary tract infection (acute cystitis) in women due to susceptible strains of *Escherichia coli* (Gram negative), and *Enterococcus faecalis* (Gram positive). The approved treatment is administration of a single oral dose, in which the active component is 3 g, given in the single dose. The minimum inhibitory concentration (MIC) of fosfomycin is 64 µg/µl or less against said bacteria (i.e., 32-128 µg/µl against *E. faecalis*, and 0.5-2 µg/µl against *E. coli*). There is use of fosfomycin outside the U.S. some more serious infections. In general, fosfomycin, and its salt forms are considered to have mild or moderate activity against Gram-positive, and/or Gram-negative microorganisms.

Figure 5:
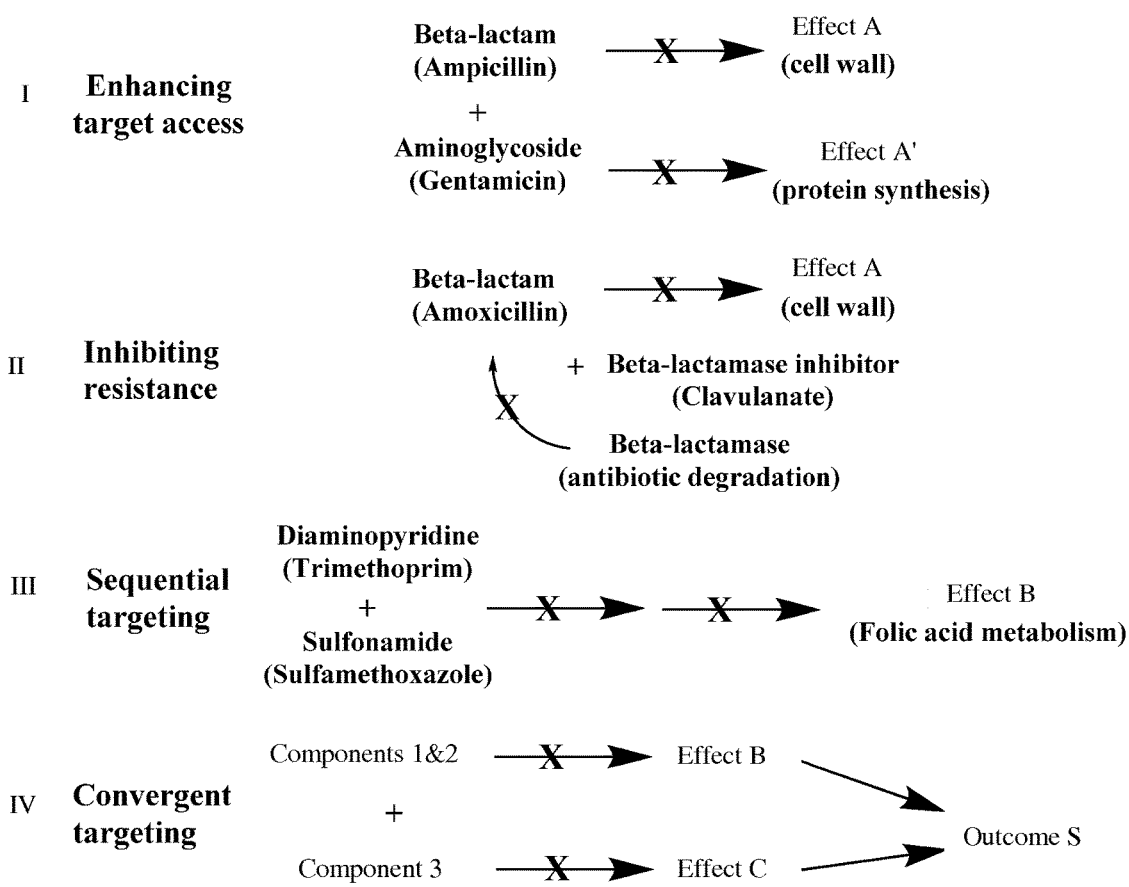
FIG. 5 depicts representative antibacterial mechanisms of activity when more than one agent is used in combination.

In some embodiments, a combination of a diaminopyridine (DP), such as a trimethoprim (2,4-diamino-5-(3,4,5-trimethoxybenzyl)pyrimidine or TMP) with a sulfonamide (SM), such as sulfamethoxazole (N1-(5-methyl-3-isoxazolyl)sulfanilamide or SMX) may form the second compound. A specific combination of trimethoprim (TMP), in combination with sulfamethoxazole (SMX) has been used in a combination approach, commonly referred to as TMP-SMX or co-trimoxazole. The two agents (TMP and SMX) act along a same pathway, in which one inhibits synthesis of a compound one-step ahead of the other in a single metabolic path, which is the typical approach when using a combination of agents. This may also be referred to as sequential targeting depicted as pathway III in FIG. 5. In this pathway, SMX inhibits the synthesis of dihydrofolate from para-aminobenzoic acid, and TMP inhibits the next step or the production of tetrahydrofolate from dihydrofolate. Such sequential targeting for antimicrobial therapy has been attempted to overcome resistance of a single agent. Unfortunately, resistance has developed with sequential targeting approaches. This is often because sequential targeting, along with other approaches, identified as enhancing target access or pathway I in FIG. 5, and inhibiting resistance or pathway II in FIG. 5, have been applied empirically in the clinic with limited mechanistic rationale, or scientifically defined foundation. When a rationale is applied, it is often typically to combine two agents acting in tandem along a same metabolic pathway (one agent inhibiting synthesis of a compound one-step ahead of another in a single metabolic path), such as with co-trimoxazole.

While activity of co-trimoxazole can be considered synergistic, resistance to co-trimoxazole also occurs with some frequency in both Gram-positive, and Gram-negative microorganisms. Resistance is also common against TMP, which can be used alone. Co-trimoxazole was approved for use in the U.S. in 1973; TMP alone was approved for use in the U.S. in 1980.

Co-trimoxazole, like fosfomycin, is generally not considered for sustained activity against severe infections. As an anti-infective, co-trimoxazole is generally used against mild or moderate (uncomplicated) infections, including, for example, infections of the urinary tract (e.g., due to susceptible strains of at least the following organisms: *Escherichia coli, Klebsiella species, Enterobacter species, Morganella morganii, Proteus mirabilis* and *Proteus vulgaris*), for bronchitis (e.g., due to susceptible strains of *Streptococcus pneumoniae*, and *Haemophilus influenzae*), and otitis media (e.g., for acute infections due to susceptible strains of *S. pneumoniae* or *H. influenzae*), skin (*Staphylococcus aureus*), with some prophylactic use against opportunistic infections (e.g., traveler's diarrhea due to susceptible strains of enterotoxigenic *E. coli*), and *Pneumocystitis jiroveci*. TMP with SMX (co-trimoxazole) has a history of use, such as providing orally, and by IV, for use including with urinary tract infections; said use providing a long safety record. Administration of co-trimoxazole in the U.S. is usually once or twice a day (every 12 hours) for up to 14 or 21 days, in which a daily dose may include 80 or 160 mg of TMP, and 400 or 800 mg of SMX, respectively (for adults). The MIC of co-trimoxazole against organisms such as *Enterobacter* species, and *H influenzae* is also less than 64 µg/µl (e.g., ≤2 µg/µl for TMP, and ≤38 µg/µl for SMX against *E. faecalis*, and ≤0.5 µg/µl for TMP, and ≤9.5 µg/µl for SMX against *H. influenzae*).

Fosfomycin is considered bactericidal (bacterial killing). SMX alone, and TMP alone are each considered bacteriostatic (bacteria inhibiting, by inhibiting metabolism of folic acid).

Unexpectedly, the combination described herein of the first compound or agent (a form of fosfomycin, its analogue, derivative, prodrug, etc., which may also be referred to herein as fosfomycin) with the second compound (comprising one or both DP, and/or SM or as a form of co-trimoxazole) has a very robust, and unexpected synergistic effect, greater than the activity of each, which is either the form of fosfomycin when used alone or is, for example, DP, and/or SM when used. The synergistic effect contradicts some literature suggesting that rapidly bactericidal agents, such as fosfomycin, producing by-products, and/or toxins that appear directly related to morbidity, may be antagonized by bacteriostatic agents. The magnitude of synergism as has been found with the described combination of a first bactericidal antimicrobial or antibiotic agent (some form of fosfomycin, its analogue, derivative, prodrug, etc.), and a second antimicrobial or antibiotic agent (one or both DP, and/or SM or as a form of co-trimoxazole) was not predicted.

The metabolic pathway affected by DP, and SM, which reversibly inhibits successive steps in folate metabolism, as depicted in FIG. 1, is not directly affected by fosfomycin. Instead, fosfomycin acts on a separate, and distinct path, blocking irreversibly peptidoglycan biosynthesis by inhibiting UDP-GlcNAc enolpyruvyl transferase (MurA). Without being bound by theory it is proposed herein that the fosfomycin pathway (in which fosfomycin has activity) is somewhat convergent with that of folate synthesis. Without being bound by theory, substrate metabolites from both pathways appear to be or are subsequently utilized as reactants in a single enzymatically-mediated chemical reaction or process. As such, a metabolite is the reactant for an enzymatic-mediated process in a second pathway, and a first antimicrobial or antibiotic that targeted the necessary pathway to produce the reactant has been combined with a second antimicrobial or antibiotic that was a specific enzyme inhibitor of the distinct reaction in the second pathway.

The above, however, does not explain additional unexpected findings in which the combination described herein, containing the fosfomycin, the sulfonamide, and/or the diaminopyridine, has also been found to have superior activity against drug resistant bacteria, including bacterial strains resistant to one or both fosfomycin, and co-trimoxazole or its components individually. In view of the findings described herein, it is believed that in a resistant organism only partial inhibition of biochemical synthesis occurs with introduction of a first inhibitor (such as the first compound or agent described herein) even though bacterial growth is not inhibited. When a second inhibitor (such as the second compound described herein), having convergent inhibitory effect, is introduced, there is concomitant partial inhibition of bacterial growth that, together, disrupts at least one essential metabolite synthesis. This is generally depicted in pathway IV or FIG. 5, in which a first component having a first target (e.g., Effect C in FIG. 5) and a second component having at least one second target (Effect B in FIG. 5) together provide an enhanced overall outcome (Outcome S in FIG. 5), which is synergistic. Thus, the composition, and combination as described herein is unique, and was found to deliver novel, and surprising effects which superseded any predicted synergistic effect. It is expected and is shown below that the spontaneous mutational frequency of bacteria (either Gram positive or Gram negative) when in the presence of the described composition (containing the fosfomycin, DP, and/or SM) is markedly lower than what is found when said agents are used alone (e.g., fosfomycin alone, co-trimoxazole alone, or TMP alone). The lower incidence of two concomitant distinct mutations—one affecting each pathway, as occurs with the unique compositions described herein—further reduce the incidence or development of new resistance. In fact, as described herein, the synergy (Outcome S, in FIG. 5) found with the described combination of the first compound or agent, and the second compound or agent not only greatly improved bacterial potency, the compositions as described herein overcame resistance, and increased the spectrum of activity, as compared with the resistance profiles, and the spectrum of activity found with independent use of the first compound or agent or the second compound or agent. The synergy was measured by known techniques, including checkerboard assay, killing curve (time-kill curve), disk diffusion, and/or kinetic spectrophotometry.

As used herein, the described composition, containing the fosfomycin, with the sulfonamide, and/or the diaminopyridine, may also include any comparable analogue, derivative or synthetic (such as so-called equivalents) of any one or more of the fosfomycin, the sulfonamide, and/or the diaminopyridine. The compositions in any of the combinations described herein may also comprise a co-administration of any one or more of the described first, and/or described second compounds or agents. The co-administration may be provided sequentially or concomitantly. The co-administration may also comprise a pre-mix of the some or all of the components as described herein. The composition may comprise a co-formulation of any one or more of the described first, and/or second compounds or agents.

In use, the described composition, containing at least two of the fosfomycin, the sulfonamide, and the diaminopyridine will, in some embodiments, be provided at dosages that differ from their independent use. For example, in the U.S., independently fosfomycin on its own is generally delivered once, in a dose that is generally 3 g (i.e., for uncomplicated urinary tract infections). At this dose, fosfomycin is only weakly bactericidal. Co-trimoxazole on its own is generally delivered twice daily, and up to four times daily, in a ratio of TMP to SMX that is 1:5, a dosing regimen that often includes a duration of at least about seven days and a maximum of about 21 days. At these current regimens, co-trimoxazole also behaves like a weak bactericidal agent. On the other hand, with the combinations described herein, the combination is strongly bactericidal, with better MIC (lower MIC for all components). With the combinations described herein, the dosing amount, and/or schedule of dosing have changed due to the synergistic effect, and significantly lower MICs when provided as the described combination. For example, at least one of the compounds when provided in the unique combination described herein (fosfomycin plus one or more of the sulfonamide, and/or the diaminopyridine) will include a lower amount of either or both the first compound (fosfomycin), and/or the second compound (sulfonamide, and/or diaminopyridine). Any of said combinations as described herein should be effective in inhibiting growth and or treating an infection caused by one or more susceptible microorganisms, including serious infections, due to an ability of the combinations described herein to achieve adequate concentrations at a site of infection. The combination as described herein should remain above the MIC of the susceptible microorganism (e.g., at the site of infection) beyond a time necessary to achieve optimal pharmacodynamic effect.

A dosing regimen of the described novel combination may include, for example, a once daily, twice daily, or up to six times per day of the described composition, in which fosfomycin is in an amount from between about 1-8 g per dose, and DP and/or SM (or as co-trimoxazole) is in an amount of between about 40 mg to 800 mg per dose. Because the combination of agents described herein has been found to have such high activity (often far greater than the compounds when used individually), the actual doses of each agent when administered to a subject in need does not need to be increased from, which avoids toxicity, and reduces adverse events. In some embodiments, the actual does of each agent when administered to a subject in need will be less than current dosing of said agents when use alone. For example, there may be a once daily, twice daily, or up to six times per day of the described composition, in which fosfomycin is in an amount from between about 1-8 g per dose, and DP and/or SM (or as co-trimoxazole) is in an amount of between about 40 mg to 800 mg per dose.

In some embodiments, a dosing regimen of the described novel combination may include one or more doses of the first compound or agent, and/or the second compound or agent currently used clinically. Said doses can also be optimized by pharmacodynamics, and pharmacokinetic data, thereby achieving a better clinical outcome in vivo as compared with outcome of said first compound or agent or second compound or agent when used independently. Said doses may be optimized to increase the AUC of the novel combination or provide an improved AUC for the novel combination, such as upon administration (oral, IV, inhalation, as examples), as compared to a same mode of administration with one of the components used individually. Said doses may be optimized to increase the AUC of the novel combination or provide an improved AUC for the novel combination, upon administration (oral, inhalation, or IV as examples), with inclusion of an effective amount of a carrier, as compared to administration using a same mode with one of the components individually, or as compared with administration using the same mode for the novel combination without said carrier. The carrier may include one or more of an effective linear chain polysaccharide, such as a cellulose, or microcrystalline cellulose, or hydroxymethyl cellulose, or hydroxypropylcellulose, or a polyvinylpyrrolidone, the carrier included in an amount that is at or less than 50% of the novel composition, or at or less than 40% of the novel composition, or at or less than 30% of the novel composition. The carrier may interact (physically, chemically, and/or transiently) with one or more of the components (first compound, and/or second compound) of the novel compositions described herein. Said dosing regimen when including current clinically useful doses for one or both of the first compound or agent, and second compounds or agent may, in many embodiments, result in an improved outcome (therapeutically, and/or clinically) as compared with outcome when only the first compound or agent or only the second compound or agent are provided independently at said (same) clinically useful dose. Further, in some embodiments, said dosing regimen when including current clinically useful doses for one or both of the independent first, and second compounds or agents may be provided to a subject having resistance or exhibiting clinical resistance to one or both of the first compound or agent, and the second compound or agent, thereby providing an improved outcome (therapeutically, and/or clinically) as compared with the outcome when only the first compound or agent or only the second compound or agent were provided independently at said (same) current clinically useful dose.

Evaluations of the described novel combination were performed in vitro against *S. aureus, E. coli, K. pneumoniae,* and *P. aeruginosa* strains, as provided in the tables below.

The described novel combination was tested against both reference, and clinically resistant strains of *S. aureus, E, coli, K. pneumoniae,* and *P. aeruginosa*. Reference and clinical isolates were obtained from the American Type Culture Collection (ATCC, Manasas, Va.) and International Health Management Associates, Inc. (Schaumberg, Ill.). Bacteria were cultured in trypticase soy broth, concentrated 10-fold by centrifugation, and cryopreserved in the same medium containing 20% glycerol by holding at −80° C. Every two weeks a small amount of frozen culture was removed aseptically, and streaked on fresh trypticase soy agar plates to act as a working inoculum. Following overnight growth at about 37° C., the plates were wrapped in parafilm, and held at about 4° C. Bacteria (4-5 colonies) were then aseptically transferred into broth growth medium for assays as needed.

Minimal inhibitory concentration (MIC) assays were performed in a manner as described for the CLSI Agar dilution or broth microdilution assay guideline (see, Clinical Laboratory Standards Institute, 2009, Methods for Dilution Antimicrobial Susceptibility Tests for Bacteria That Grow Aerobically; Approved Standard, Eighth Edition, M07-A8, Vol. 29, No. 2). For example, known antibiotics or the compositions described herein were dissolved, serially diluted, and then added to tempered molten Mueller-Hinton Agar before pouring of plates; or were dissolved, and then serially diluted in 100 μL cation-adjusted Mueller-Hinton broth across the assay plate in the classical 2-fold geometric format. D-glucose-6-phosphate was included as a medium supplement in both agar, and broth at a concentration of 50 mg/L. Antibiotic concentrations for agar assay were at the final concentration. Antibiotic concentrations for broth microdilution in each well at this point were double what the final assay concentration would be. Bacterial inocula were prepared by swabbing several colonies from a fresh agar plate, and resuspending the bacteria to a density that was the 0.5 McFarland turbidity standard, considered close or equivalent to $1 \times 10^8$ CFU/mL. For agar dilution, a steers replicator was utilized to deliver $1 \times 10^4$ CFU/spot. For broth microdilution, the bacterial inocula were diluted in the cation-adjusted Mueller-Hinton broth to $1 \times 10^6$ CFU/mL, and 100 μL was overlayered onto the wells containing a diluted antibiotic or a composition described. Following incubation as per the guideline, results were recorded as growth or no growth, and the lowest concentration of the antibiotic or the composition described where no growth was observed was declared the MIC.

To assay for synergy of antibacterial combinations, a recognized synergy checkerboard assay, adapted from the CLSI guideline microdilution assay, was utilized (see Eliopoulos, G. M., and Moellering, R. C, Jr., 1996. Antimicrobial Combinations, pg. 330-396. In: Lorian, V. (Ed.), Antibiotics in Laboratory Medicine, 4$^{th}$ Ed., Williams & Wilkins; Baltimore, Md.). In the case of the agar dilution method, each antibiotic alone, or in combination, was added to agar prior to plate pouring. For broth microdilution, the first compound (or antibiotic or agent) was diluted in cation-adjusted Mueller-Hinton broth across the plate along the horizontal axis with each well in a row containing 50 μL of an identical concentration of compound (or antibiotic). Along the vertical axis a dilution series of the second compound (or antibiotic) was dispensed. At this point the drug concentrations are four-fold of the final desired working concentration. The bacterial inoculum is prepared as described above for the MIC assay, and 100 μL of culture is overlayered onto the combined compound (or antibiotic) matrix. Following incubation, wells with no growth are noted. The fractional inhibitory concentration (FIC), which provides the mathematical definition (as shown below) is calculated to determine whether there was synergy, or the MIC concentrations for fosfomycin, and trimethoprim for the combination were utilized for the calculation because the MIC for trimethoprim is commonly utilized to represent the value, and susceptibility of bacteria isolates to co-trimoxazole.

FIC=(MIC-A combination/MIC-A alone)+(MIC-B combination/MIC-B alone).

In the above, FIC: Synergy=FIC ≤0.5; Additive= FIC >0.5-1; Indifferent=FIC >1-2; Antagonism=FIC >2-4.

Synergy was also assayed by both agar, and broth microdilution methods. Additional information gathered about the synergistic effect of the described composition as a combination therapy was evaluated by determining bacterial killing effect. This was performed as described above for the checkerboard synergy assay with the exception that the bacterial count in an assay well was determined by plating at the beginning of the experiment, and identifying at the end of incubation for an assay well where growth was inhibited. This has been adapted from both the broth microdilution, and the bactericidal assays (Clinical Laboratory Standards Institute (1999) Methods for Determining Bactericidal Activity of Antimicrobial Agents; Approved Guideline M26-A, Vol. 19, No. 18). One additional difference from the guideline assay was that the starting inoculums were $5 \times 10^5$ CFU/mL as per the MIC assay instead of $1 \times 10^6$ CFU/mL in the guideline minimal bactericidal concentration assay. The value derived was the reduction in bacterial numbers (viability) for the compounds when alone versus the described composition comprising the combined antibiotics.

Synergism was found using the checkerboard microdilution assay, in which synergy was considered as a four-fold reduction in MIC. In fact, the synergistic effect of the described composition on all isolates was as much as an 8-fold reduction or as much as a 16-fold reduction. FIC values were ≤0.5.

Bactericidal synergy was demonstrated by determining the minimal bactericidal concentration, ≥3 log 10 reduction was observed for the combination ranging from 2-fold to as much as 266-fold reduction in concentrations of the individual agents.

Similarly, bactericidal synergy was greater than the defined value of ≥3 $\log_{10}$ change in viable count assessed by a time-kill assay after 24 hours.

The time kill assay was performed sequentially to the checkerboard synergy studies. Fifty milliliter Erlenmeyer flasks containing 10 mL of pre-warmed sterile cation-adjusted Mueller-Hinton Broth with or without antibiotic or the composition described herein were inoculated with bacteria to a starting level of $1 \times 10^6$ CFU/mL, followed by incubation at 37° C. with shaking (~200 rpm). At various time points, aliquots were withdrawn, serially diluted in antibiotic-free broth medium, and 0.1 mL aliquots of each dilution were spread plated on Trypticase soy agar plates. Enumeration was by counting colonies after 24-hours further incubation of the plates at 37° C., and calculating the reduction in viable bacteria.

The unique reduction in spontaneous mutational frequency, an indicator of the potential to experience lessened pre-existing antibiotic resistance from a bacterial population, was evaluated for the composition combination described herein, as well as for the fosfomycin and co-trimoxazole individually. To perform this study, a bacterial inoculum was prepared as described above for the minimal inhibitory concentration assay, and viable bacteria level confirmed by plate count, and 0.1 mL aliquots ($1 \times 10^9$ CFU/mL) of the bacteria were spread plated onto up to 500 Trypticase soy agar plates containing 4-fold MIC of the combination or 2-fold MIC or each antibiotic (fosfomycin or co-trimoxazole) alone providing a cumulative bacterial population of approximately $1\times10^{10}$ in order to afford detection of a low resistance frequency. Following 24-hour incubation at 37° C., any colonies that grew up as suspect resistant mutants were streaked onto fresh agar plates of the same composition combination or antibiotic containing media to confirm resistance. MIC was further evaluated to confirm resistance, and the spontaneous mutational frequency was calculated based on the following equation:

$$\frac{\text{(Numbers of viable resistant bacterial cells)}}{\text{(Total numbers of viable bacterial cells inoculated)}}. \tag{1}$$

The MIC (in µg/ml), and the fractional inhibitory concentration (FIC) of novel combination described herein against a wide variety of microorganisms, including Gram positive, and Gram negative bacteria presenting as clinically resistant, are provided in TABLE 1, demonstrating synergy, using a broth checkerboard assay, in which the novel composition described herein (Combo) was compared with each of the first compound or agent (as fosfomycin), and the second compound (as DP, and SM) when used alone. In TABLE 1, the second compound was a known DP and SM combination of trimethoprim and sulfamethoxazole or co-trimoxazole (in which data represents their independent MICs), and the Combo was the fosfomycin with the DP, and SM of the second compound. For FIC, synergy (S) was 0.5; additive (A) was ≥0.5-1; indifferent (I) was >1-2; and antagonistic (X) was >2. Bacterial strains resistant to antibiotics (*) as noted were based on reported CLSI susceptibility breakpoints: Fosfomycin, ≤64 µg/ml, 5; co-trimoxazole, ≤2/38 µg/ml, S.

In view of TABLE 1, clinically relevant broad spectrum synergy was demonstrated for a composition comprising the first compound and the second compound, in which the described composition was effective against bacterial strains, including strains resistant to one or both of the trimethoprim, and the sulfamethoxazole. Additional synergy is identified in TABLE 2 (utilizing the broth checkerboard assay) and TABLE 3 (utilizing the agar checkerboard assay) for *E. coli*; TABLE 4 (utilizing the broth checkerboard assay) and TABLE 5 (utilizing the agar checkerboard assay) for *K. pneumonia*; TABLE 6 (utilizing the broth checkerboard assay) and TABLE 7 (utilizing the agar checkerboard assay) for *P. aeruginosa*. In these analyses, for FIC, synergy (S) was ≤0.5; additive (A) was >0.5-1; indifferent (I) was >1-2; antagonistic (X) was >2); and certain bacterial strains (*) were resistant to antibiotics as noted based on reported CLSI susceptibility breakpoints: fosfomycin <64 µg/ml, S; co-trimoxazole <2/38 µg/ml, S. MIC comparator data was performed using the following known antibiotics: Amoxicillin/clavulanic acid, Cefoxitin, Cefotaxime, Ceftazidime, Ceftriaxone, Piperacillin, Ampicillin, Merropenem, Polymixin B, Tobramycin, Amikacin, Ciprofloxacin (data not shown). The strains of *E. coli* in the comparator analyses included extended spectrum beta-lactamase (ESBL) producers based on phenotype (e.g., Amoxicillin/clavulanic acid resistance, or Cefoxitin resistance), as well as carbapenem resistant, or quinolone resistant (15 strains). Strains of *K. pneumonia* in the comparator analyses were highly resistant to many of the clinical comparators, a number of these strains express ESBLs based on phenotype, and several were carbapenem, and quinolone resistant. Strains of *K. pneumonia* in the comparator analyses were highly resistant to commonly utilized clinical comparators, including $3^{rd}$-generation cephalosporins, carbapenems, aminoglycosides, and quinolones.

TABLE 1

| Bacteria | Combo (µg/ml) (F/DP/SM) (µg/ml) | Fosfomycin (F) (first compound) (µg/ml) | DP/SM (second compound) (µg/ml) | FIC |
|---|---|---|---|---|
| *Staphylococcus aureus* (ATCC 29213 - MSSA) | 0.25/0.125/2.38 | 32 | 0.5/9.5 | 0.26 |
| *Staphylococcus aureus* (ATCC 33591) | 8/0.25/4.75 | 64 | 2/38 | 0.25 |
| *Staphylococcus aureus* (MGH-04) | 32/1/19 | 128* | 4/76* | 0.5 |
| *Staphylococcus aureus* (918019 - MRSA) | 4/0.125/2.38 | 32 | 0.5/9.5 | 0.38 |
| *Staphylococcus aureus* (959797 - MRSA) | 2/0.25/4.75 | 16 | 2/38 | 0.25 |
| *Staphylococcus aureus* (USA-300 CDC - MRSA) | 16/0.125/2.38 | 64 | 0.5/9.5 | 0.5 |
| *Enterococcus faecalis* (MGH-01) (VanA) | 64/2/38 | 256* | >8/152* | ≤0.38 |
| *Enterococcus faecalis* (MGH-06) | 32/0.5/9.5 | 128* | 4/76* | 0.38 |
| *Enterococcus faecalis* (ATCC 29212) | 16/0.25/4.75 | 64 | 1/19 | 0.5 |
| *Escherichia coli* (ATCC 25922) | 0.03/0.125/2.38 | 8 | 0.5/9.5 | 0.25 |
| *Escherichia coli* (854535) | 16/2/38 | 64 | 8/152* | 0.5 |
| *Escherichia coli* (928017) | 16/0.03/0.6 | 64 | 0.25/4.75 | 0.38 |
| *Pseudomonas aeruginosa* (924190) | 32/2/38 | 256* | 4/76* | 0.63 |
| *Pseudomonas aeruginosa* (985543) | 32/0.5/9.5 | 128* | 2/38 | 0.5 |

TABLE 2

| Escherichia coli | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 846439 | 8/0.25/4.75 | 32 | >4/76* | ≤0.28 | S |
| 846446 | 0.25/0.06/1.25 | 2 | >4/76* | <0.13 | S |
| 846450 | 4/2/38 | 16 | >4/76* | ≤0.5 | S |
| 857021 | 8/2/38 | 32 | >4/76* | ≤0.5 | S |
| 863686 | 8/2/38 | 32 | >4/76* | ≤0.5 | S |

TABLE 3

| Escherichia coli | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 846439 | 16/0.5/9.5 | 64 | 8/152* | 0.31 | S |
| 846446 | 1/0.125/2.38 | 4 | 8/152* | 0.26 | S |
| 846450 | 8/2/38 | 32 | 8/152* | 0.5 | S |
| 846455 | 4/1/19 | 128* | 4/76* | 0.28 | S |
| 847149 | 16/1/19 | 128* | 4/76* | 0.38 | S |
| 854535 | 64/1/19 | 128* | 4/76* | 0.75 | A |
| 854566 | 4/1/19 | 128* | 4/76* | 0.28 | S |
| 857021 | 16/2/38 | 64 | 8/152* | 0.5 | S |
| 863078 | 4/1/19 | 128* | 4/76* | 0.28 | S |
| 863686 | 16/2/38 | 64 | 16/304* | 0.38 | S |
| ATCC 25922 | 0.12/0.25/4.75 | 16 | 1/19 | 0.26 | S |

TABLE 4

| K. pneumoniae | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 848788 | ND | >64* | >4/76* | ND | ND |
| 857147 | 4/0.06/1.19 | 16 | >4/76* | ≤0.26 | S |
| 857187 | 32/0.5/9.5 | 64 | 1/19 | 1 | I |
| 868968 | 32/4/76; 64/.05/9.5 | >64* | >4/76* | ND | ND |
| 868972 | 32/4/76 | 64 | >4/76* | ND | ND |
| 869028 | ND | >64* | >4/76* | ND | ND |
| 875638 | 16/2/38 | 32 | >4/76* | ≤0.75 | A |
| 892483 | ND | >64* | >4/76* | ND | ND |
| 926439 | 32/0.125/2.38 | 64 | 0.25/4.75 | 0.75 | A |

TABLE 5

| K. pneumonia | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 848788 | 64/1/19 | 256* | 16/304* | 0.31 | S |
| 857147 | 8/0.125/2.38 | 32 | 16/304* | 0.26 | S |
| 857187 | 32/1/19 | 128* | 2/38 | 0.75 | A |
| 868968 | 64/2/38 | 256* | 16/304* | 0.38 | S |
| 868972 | 64/2/38 | 128* | 16/304* | 0.63 | A |
| 869028 | 64/2/38 | 256* | 16/304* | 0.38 | S |
| 870964 | 128/1/19 | 256* | 4/76* | 0.75 | A |
| 875638 | 16/2/38 | 64 | 16/304* | 0.38 | S |
| 892483 | 64/2/38 | 256* | 16/304* | 0.38 | S |
| 926439 | 32/0.125/2.38 | 128* | 0.5/9.5 | 0.5 | S |

TABLE 6

| P. aeruginosa | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 826882 | 16/0.25/4.75 | 64 | >4/76* | ≤0.28 | S |
| 880238 | 16/1/19 | 64 | >4/76* | ≤0.38 | S |
| 906939 | 8/2/38 | 64 | >4/76* | ≤0.38 | S |
| 926474 | 8/1/19 | 32 | >4/76* | ≤0.38 | S |
| 945543 | 16/0.125/1.19 | 32 | 0.125/1.19 | 1.5 | I |
| 945545 | 8/2/38 | 64 | >4/76* | ≤0.38 | S |
| 945748 | 16/0.5/9.5 | 64 | >4/76* | ≤0.31 | S |

TABLE 7

| P. aeruginosa | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 826882 | 32/0.5/9.5 | 128* | 16/304* | 0.28 | S |
| 880238 | 32/1/19 | 128* | 16/304* | 0.31 | S |
| 889058 | 4/1/19 | 128* | 4/76* | 0.28 | S |
| 906939 | 16/2/38 | 128* | 16/304* | 0.25 | S |
| 926474 | 16/2/38 | 64 | 16/304* | 0.38 | S |
| 914881 | 4/1/19 | 128* | 4/76* | 0.28 | S |
| 924190 | 64/2/38 | 256* | 8/152* | 0.5 | S |
| 945543 | 4/1/19 | 128* | 4/76* | 0.28 | S |
| 945545 | 16/2/38 | 128* | 16/304* | 0.25 | S |
| 945748 | 32/0.5/9.5 | 128* | 8/152* | 0.31 | S |
| PAO1 | 4/0.5/9.5 | 32 | 2/38 | 0.38 | 5 |

Further synergy is identified in TABLE 8 (utilizing the broth checkerboard assay) against uUTI species. In these analyses FIC, synergy (S) was ≤0.5; additive (A) was >0.5-1; indifferent (I) was >1-2; antagonistic (X) was >2); and certain bacterial strains (*) were resistant to antibiotics as noted based on reported CLSI susceptibility breakpoints: fosfomycin ≤64 µg/ml, S; co-trimoxazole ≥2/38 µg/ml, S. Synergy was demonstrated with the novel combination described herein including synergistic activity against a preponderance of Proteus mirabilis, Staphylococcus saprophyticus, and Enterococcus faecalis strains. MIC comparator data was performed using the following known antibiotics: Nitrofurantoin, Fosfomycin, Co-trimoxazole, and Levofloxacin.

TABLE 8

| | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| P. mirabilis | | | | | |
| 1128681 | 1/0.0075/0.15 | 4 | 0.06/1.19 | 0.38 | S |
| 1124256 | 16/0.5/9.5 | 64 | 2/38 | 0.5 | S |
| 1184042 | 1/0.015/03 | 4 | 0.06/1.19 | 0.5 | S |
| 1071120 | 0.25/0.06/1.19 | 1 | 0.25/4.75 | 0.5 | S |
| S. saprophyticus | | | | | |
| 1124324 | 8/0.125/2.38 | 32 | 0.5/9.5 | 0.5 | S |
| 1119421 | 8/0.125/2.38 | 32 | 0.5/9.5 | 0.5 | S |
| 1136894 | 16/0.125/2.38 32/≤0.06/1.19 | 64 | 0.25/4.75 | ≤0.75 | A |

TABLE 8-continued

| | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| E. faecalis | | | | | |
| 10864321 | 0.125/0.5/9.5 | 32 | >8/152* | ≤0.04 | S |
| 1175598 | 8/2/38 | 32 | >8/152* | ≤0.38 | S |
| 1120278 | 8/0.25/4.75 | 64 | 0.5/9.5 | 0.63 | A |
| 1082155 | 8/2/38 | 32 | >8/152* | 0.38 | S |
| 1129099 | 1/0.125/2.38 2/≤0.06/1.19 | 4 | 0.25/4.75 | ≤0.75 | A |

Synergy is also identified in TABLE 9 (utilizing the agar checkerboard assay) against *N. gonorrhoeae*. In these analyses, the agar dilution was performed utilizing GC agar supplemented with Isovitalex, and 50 mg/L of D-glucose-6-phosphate. The FIC, synergy (S) was ≤0.5; additive (A) was >0.5-1; indifferent (I) was >1-2; antagonistic (X) was >2); and certain bacterial strains (*) were resistant to antibiotics as noted based on reported CLSI susceptibility breakpoints: fosfomycin ≤64 µg/ml, S; co-trimoxazole ≤2/38 µg/ml, S. Synergy was demonstrated as well as an additive effect with the novel combination described herein against gonococci. MIC comparator data was performed using the following known antibiotics: Ceftriaxone, Azithromycin, Cefixime, Ciprofloxacin, Tetracycline, Pristinamycin, Solithromycin, and Delafloxacin. Pristinamycin was purified from capsules obtained in France; Solithromycin, and Delafloxacin were synthesized internally for comparison.

TABLE 9

| N. gonorrhoeae | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 127781 | 4/0.5/9.5 | 16 | 1/19 | 0.75 | A |
| 127782 | 4/0.25/4.75 | 16 | 1/19 | 0.5 | S |
| 127783 | 4/0.5/9.5 | 16 | 1/19 | 0.75 | A |
| 127786 | 4/0.25/4.75 | 16 | 0.5/9.5 | 0.75 | A |
| 1117522 | 4/0.25/4.75 | 16 | 0.5/9.5 | 0.75 | A |
| 1117523 | 4/0.125/2.38 | 16 | 1/19 | 0.38 | S |
| 1117524 | 2/0.25/4.75 | 8 | 1/19 | 0.5 | S |
| 1117525 | 4/0.25/4.75 | 8 | 0.5/9.5 | 1 | A |
| 1117527 | 2/0.5/9.5 | 8 | 2/38 | 0.5 | S |

Synergy was further demonstration using the broth checkerboard assay in TABLE 10 showing MIC for MRSA strains of *S. aureus*, many of which are associated with skin and skin structure infection (SSSI), and acute bacterial SSSI (ABSSSI). The breadth of the synergy against MRSA with the novel combination described herein is supportive of an ABSSSI indication. In these analyses FIC, synergy (S) was ≤0.5; additive (A) was >0.5-1; indifferent (I) was >1-2; antagonistic (X) was >2); and certain bacterial strains (*) were resistant to antibiotics as noted based on reported CLSI susceptibility breakpoints: fosfomycin ≤64 µg/ml, S; co-trimoxazole ≤2/38 µg/ml, S.

TABLE 10

| S. aureus | Combo (ug/ml) (F/DP/SM) (µg/ml) | Fosfomycin (F) (first compound) (µg/ml) | DP/SM (second compound) (µg/ml) | FIC | Synergy S/A/I/X |
|---|---|---|---|---|---|
| 829025 | 1/0.015/0.3 | 4 | 0 . . . 06/1.19 | 0 . . . 5 | S |
| 829049 | 2/0.015/0.3 | 8 | 0 . . . 06/1.19 | 0.5 | S |
| 903887 | 2/0.015/0.3 | 8 | 0 . . . 06/1.19 | 0.5 | S |
| 920516 | 0.25/0.0078/0.15 | 2 | 0 . . . 06/1.19 | 0.5 | S |
| 920962 | 0.5/0.015/0.3 | 2 | 0.125/2.38 | 0.25 | S |
| 927596 | 2/0.03/0.6 | 8 | 0.125/2.38 | 0.38 | S |
| 938125 | 0.5/0.0078/0.15 | 4 | 0 . . . 06/1.19 | 0.5 | S |
| 953041 | 1/0.03/0.6 | 8 | 0.25/4.75 | 0.25 | S |
| 956270 | 0.5/0.015/0.3 | 28 | 0 . . . 06/1.19 | 0.5 | S |
| 956362 | 4/0.015/0.3 | 16 | 0 . . . 06/1.19 | 0.5 | S |
| 967287 | 2/0.0039/0.078 | 8 | 0 . . . 06/1.19 | 0.32 | S |
| 974980 | 2/0.03/0.6 | 8 | 0.125/2.38 | 0.5 | 5 |
| 979234 | 4/0.0078/0.15 | 16 | 0 . . . 06/1.19 | 0.38 | S |
| 1045190 | 0.5/0.015/0.3 | 2 | 0 . . . 06/1.19 | 0.5 | S |

With the novel combination described herein, the bactericidal (killing) synergy was demonstrated against all strains shown in TABLE 11. As there is no published definition for bactericidal synergy, MIC metric was utilized. For the minimal bactericidal concentration (MBC, µg/ml), TABLE 11 shows the lowest concentration providing a ≥3-log reduction within 24 hours of the first compound, the second compound, and the novel combination described herein.

TABLE 11

| Bacteria | Combo (µg/ml) (F/DP/SM) (µg/ml) | Fosfomycin (F) (first compound) (µg/ml) | DP/SM (second compound) (µg/ml) |
|---|---|---|---|
| Staphylococcus aureus (ATCC 29213 - MSSA) | 1/0.5/9.5 | 128 | 2/38 |
| Staphylococcus aureus (ATCC 33591) (MRSA) | 32/1/19 | 256 | 8/152 |
| Staphylococcus aureus (MGH-04) | 128/4/76 | 256 | 16/304 |
| Staphylococcus aureus (918019 - MRSA) | 16/0.5/9.5 | 128 | 2/38 |
| Staphylococcus aureus (959797 - MRSA) | 8/1/19 | 64 | 8/152 |
| Staphylococcus aureus (USA-300 CDC - MRSA) | 16/0.5/9.5 | 256 | 2/38 |

TABLE 11-continued

| Bacteria | Combo (μg/ml) (F/DP/SM) (μg/ml) | Fosfomycin (F) (first compound) (μg/ml) | DP/SM (second compound) (μg/ml) |
|---|---|---|---|
| Enterococcus faecalis (MGH-01) (VanA) | 128/4/76 | ≥512 | >16/304 |
| Enterococcus faecalis (MGH-06) | 64/1/19 | 512 | 16/304 |
| Enterococcus faecalis (ATCC 29212) | 64/4/76 | ≥512 | >8/152 |
| Escherichia coli (ATCC 25922) | 0.12/0.5/9.5 | 32 | 2/38 |
| Escherichia coli (854535) | 64/8/152 | 256 | >8/152 |
| Escherichia coli (928017) | 64/0.25/4.75 | 256 | 2/38 |
| Pseudomonas aeruginosa (924190) | 64/4/76 | >512 | >8/152 |
| Pseudomonas aeruginosa (985543) | 128/2/38 | 512 | 8/152 |

Figure 2:
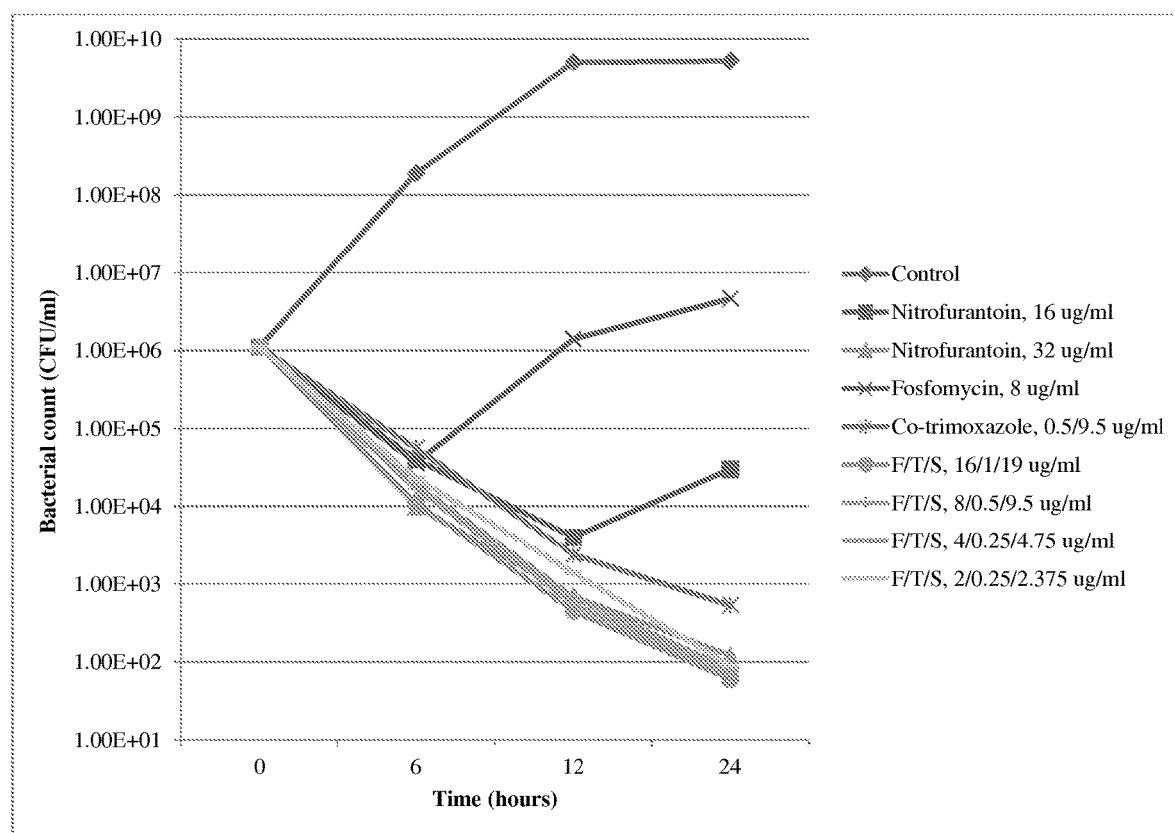
FIG. 2 depicts a representative in vitro time-kill graph of the described composition on a known strain of E. coli as compared with alternative and individual antibiotic agents.
Figure 3:
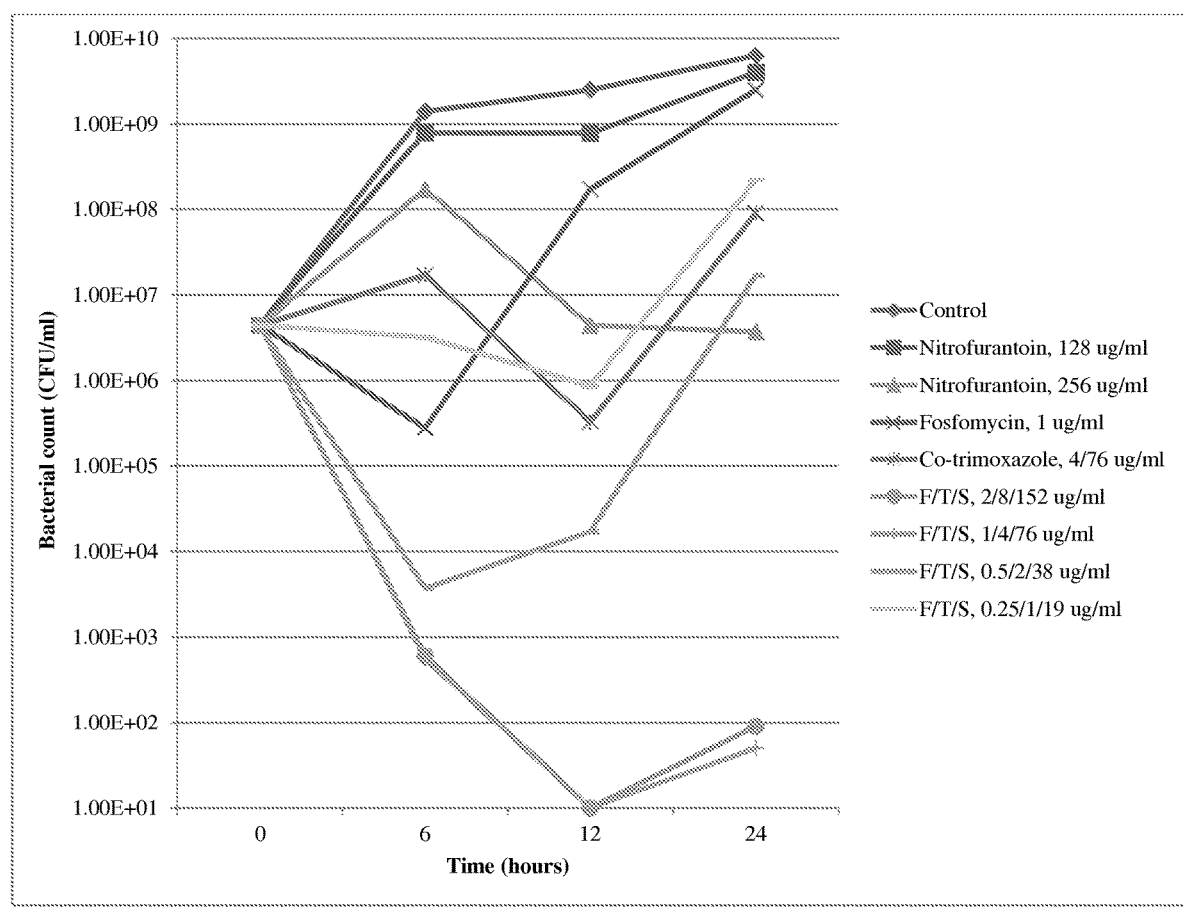
FIG. 3 depicts a representative in vitro time-kill graph of the described composition on a known nitrofurantoin-resistant strain of E. coli as compared with alternative and individual agents.
Figure 4:
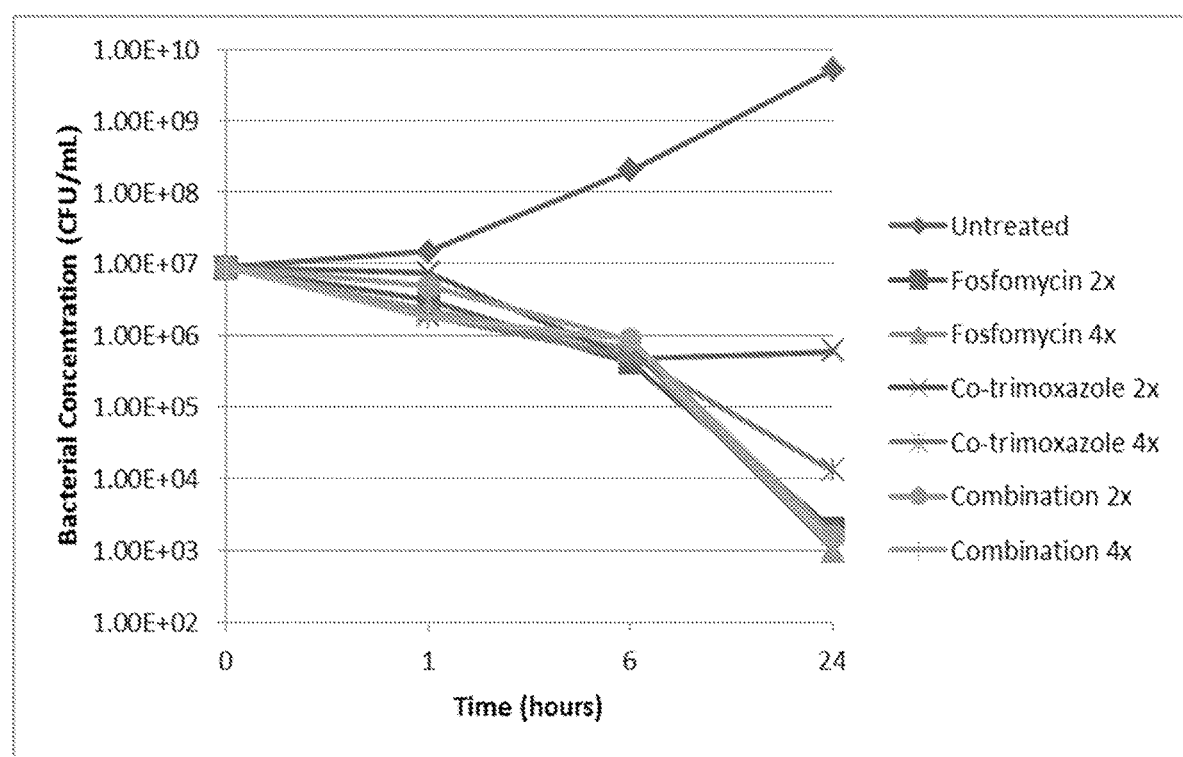
FIG. 4 depicts a representative in vitro time-kill graph of the described composition on a known strain of S. aureus as compared with alternative and individual antibiotic agents.

Bactericidal killing is demonstrated in FIGS. 2-4, against E. coli (FIG. 2), nitrofurantoin-resistant E. coli (FIG. 3), and S. aureus (FIG. 4). Antibiotic concentrations for E. coli (FIG. 2) were: fosfomycin 2× (16 μg/ml), 4× (32 μg/ml); co-trimoxazole 2× (1/19 μg/ml), 4× (2/38 μg g/ml); and the novel combination 2× (4/0.25/4.75 μg/ml), and 4× (8/0.5/9.5 μg/ml). Antibiotic concentrations for S. aureus (FIG. 4) were: fosfomycin 2× (64 μg/ml), 4× (128 μg/ml); co-trimoxazole 2× (1/19 μg/ml), 4× (2/38 μg/ml); and the novel combination 2× (16/0.25/4.75 μg/ml), and 4× (32/0.5/9.5 μg/ml).

The described novel compositions (said combination of a first and second compounds or agents) were found to exhibit a synergy, and a growth inhibition well below breakpoint values. The unexpected values show synergy at unpredicted levels. Resistant breakpoints for the above first compound and second compound are provided below in TABLE 12, the data is based on CLSI MIC breakpoint data (i.e. from the Clinical Laboratories Standards Institute) in comparison with data obtained from the European Committee on Antimicrobial Susceptibility Testing (EUCAST).

TABLE 12

| | Resistance breakpoints (μg/ml) | |
|---|---|---|
| | Fosfomycin | DP with SM |
| CLSI | ≥256 | ≥4/76 |
| EUCAST | >32 | >4/76 |

Synergy with utilization of the composition described herein was found against both Gram negative bacteria, and Gram positive bacteria, which has not been found by other antimicrobial agents or combinations of antibiotic agents. In fact, the novel compositions described herein were effective against the most common Gram negative, and Gram positive bacteria independent of their resistance. In some embodiments, an FIC Index value was in the range of about 0.02 to 0.4 for E. coli, K. pneumoniae, and P. aeruginosa. The FIC Index value was in a range of about 0.07-0.25 for S. aureus. Synergy was found against S. aureus, including resistant strains of S. aureus, such as MRSA, which is a significant microorganism in hospital acquired bacterial pneumonia. Further, the novel compositions described herein were active against strains that are resistant to the independent compounds that make up the composition when used on their own. As such, the novel compositions described herein are able to overcome the resistance problems previously found with utilization of its constituent components.

While the susceptibility breakpoint is 64 for fosfomycin alone and is 4/76 for a trimethoprim/sulfamethoxazole combination (e.g., when provided as co-trimoxazole), with the combinations described herein and as exhibited in the tables, MICs are at least four- to eight-fold below these breakpoints. To provide sustained and/or acceptable exposures of the combination described herein, it may, in some embodiments, be that fosfomycin is provided in an amount so as to have a concentration above 64 μg/μl, at least for about 70% of the time, or for greater than 70% of the time. Similarly, it may be, in some embodiments, that the diaminopyridine (or its peak) is between about 5 and about 10 μg/μl, at least when administered, and/or for some time thereafter. An example, the diaminopyridine may be above the MIC for about or greater than about 50% of the time. Taking the above into account, in a first example, a dosing regimen of a combination described herein may include about 1 g of fosfomycin, given three times per day (about 1 g per dose), with at least one of the diaminopyridine provided three times per day (at about 110 mg per dose), and/or the sulfonamide provided three times per day (at about 550 mg per dose).

The described composition is able to reduce the MIC below the clinical breakpoints found for the individual components. This enables use of the novel compositions described herein against otherwise multi-drug resistant bacteria, including multi-drug resistant E. coli, multi-drug resistant P. aeruginosa, and multi-drug resistant S. aureus, as examples. Thus, with the described combinations and the low MIC values (low MIC within a "susceptible" range, and/or low MIC that is well below the accepted "susceptible" range) there will be better outcomes. With the number of strains, and types of strains showing susceptibility to the combinations described herein, lower doses (of each component, or of one or more of the components) will be possible with the combinations described herein (e.g., for treatment against, killing of, and/or inhibition of growth of the susceptible microorganisms). With the number of strains, and types of strains, showing susceptibility to the combinations described herein, shortened treatment duration (of each component, or of one or more of the components) will be possible with the combinations described herein (e.g., for treatment against, killing of, and/or inhibition of growth of the susceptible microorganisms). With the number of strains, and types of strains, showing susceptibility to the combinations described herein, a shorter median time to defervescence will be possible with the combinations described herein (when administered for treatment against, killing of, and/or inhibition of growth of the susceptible microorganisms).

With the described composition using the first compound and the second compound, such as ones identified in the tables, the frequency of spontaneous mutants resistant to said novel composition was representatively assessed, and found to be $\leq 1.8 \times 10^{-10}$ as compared with $6.33 \times 10^{-6}$ for fosfomycin alone or $2.67 \times 10^{-9}$ for co-trimoxazole alone or $3.40 \times 10^{-8}$ for nitrofurantoin. The spontaneous mutational frequency (SMF; resistance) was calculated as the number of resistant colonies observed divided by the total inoculum. The substantially lower SMF for the novel combination described herein indicates a lower potential for resistance evolution as compared with the individual components, or the nitrofurantoin comparator. Without being bound by theory, it is suggested that in addition to the substantially lower SMF and in view of the synergy described herein, susceptibility breakpoints with the described compositions may not have to change significantly over time. In some embodiments, susceptibility breakpoints with the described compositions will not have to change significantly.

With the described compositions, and without being bound by theory, but in view, in part on the substantially lower SMF, and, in part, on the synergy, there will be an infrequent selection of resistant bacterial strains with the combinations described herein. The infrequent selection will also be infrequent at even low concentrations of the combinations described herein.

With the described novel compositions an $MIC_{90} \leq 16$ μg/mL was identified for certain important Gram negative bacteria. For such strains, a representative dosing regimen of the novel composition against, for example, *E. coli* strains, such as those tested in the tables above may include 0.03-16 μg/mL of the first compound, and 0.61-38 μg/mL, and 0.03-2 μg/mL of the second compound, which comprises two individual components of DP, and SM.

With the described novel compositions MICs ≤64 μg/mL were identified for other, and most of the remaining important Gram negative bacteria. For such strains, a representative dosing regimen of the novel composition against, for example, *P. aeruginosa* strains, such as those tested in the tables above may include 2-32 μg/mL of the first compound, and 0.125-2 μg/mL, and 0.219-38 μg/mL of the second compound, which comprises two individual components of DP, and SM.

In view of prior safety analysis for components that may make up the compositions described herein, the combinations described herein will likely include amounts or doses of each of the components that are about or less than the amounts or doses of each of the components (when used individually) found to be safe when provided to a subject in need thereof.

As shown, the combination described herein provides excellent Gram-positive activity, and Gram-negative activity, thereby offering a broadened spectrum, with synergistic potency. Further, the combination described herein provides efficacy against a wide variety of infectious organisms, including parasites. The combination may be selected to have a therapeutic effect based on the sulfonamide(s) and/or the diaminopyridine(s) that are in the combination, in which certain sulfonamides and/or diaminopyridines exhibit greater or lesser anti-parasitic activity in addition to their antibacterial activity. The combination described herein is effective against strains resistant to one or more of the components in the described composition. The combination described herein is effective against strains resistant to existing drugs or agents that are currently used with some effectiveness in certain individuals in need thereof. The spectrum of activity, as provided with the described composition, is supportive of use with many infections, such as those of the urinary tract, respiratory tract, and skin and skin structures, including acute bacterial skin and skin structure infections, and sexually transmitted infections, and related infections or diseases. The bactericidal activity as provided with the described composition is supportive of use at reduced concentrations as compared with current use of the independent components when used for current indications as an antibiotic for bacterial infections, including infections of the urinary tract, respiratory tract, and skin a skin structure, including acute bacterial skin, and skin structure infections, and certain sexually transmitted diseases, and related infections. The very low frequency of spontaneous mutational frequency with the combination described herein is highly indicative of a much reduced potential for resistance with the compositions described herein. In some embodiments, the described combination may be administered in a lower dose while still providing efficacy. In some embodiments, the described combination may be administered at a higher dose while remaining safe for use. In one or more embodiments, the described combination provides an improved therapeutic index of the combination while not enhancing general toxicity.

Without being bound by theory, the synergism found with the novel compositions described herein may be related to specific inhibition of peptidoglycan (cell wall) synthesis in addition to a synergistic inhibition of a pathway leading to essential metabolites necessary for peptidoglycan synthesis rendering bacteria or other microorganisms highly susceptible to the novel compositions disclosed herein. In view of said mechanism of action of said novel composition, said novel composition should be effective against many or most clinically relevant Gram negative bacteria as well as Gram positive bacteria independent of the bacterial resistance profiles. Further, it is expected that there will be a reduced risk of use with said novel compositions in view of their known safety profiles showing they are well tolerated, and have safe usage when provided individually. Moreover, with lower dosing levels, as may be provided with the novel compositions described herein, there will be fewer safety concerns. A favorable spectrum against other multidrug resistant Gram negative, and Gram positive bacteria is provided and expected to be due in part to the highly synergistic interaction found with the novel composition described herein.

Providing the combination as described above, such as sequentially, or concomitantly, to a subject in need will preferably include providing all the components of the composition so that there is overlapping exposure with regard to each of the components. Providing the combination as described will preferably include having each of the components in sufficient amounts at a similar schedule or an overlapping schedule (same or overlapping times), or at or near maximal amounts at a similar a schedule or an overlapping schedule (same or overlapping times), whether or not the components are in a same formulation.

In one or more embodiments, a formulation, or the combination as described herein, may be provided once a day. In some embodiments, a formulation, or the combination as described herein may be provided twice daily. In one or more embodiments, a formulation, or the combination as described herein may be provided three times a day. In one or more embodiments, a formulation, or the combination as described herein may be provided four times a day, or at least one of the components is provided up to four times per day. Fosfomycin, having a short half-life, may, in some embodiments, be provided more than once per day, or at least in divided doses, two times a day, or three time a day, or four times a day. In one or more embodiments, a total daily amount of the fosfomycin may be in an amount in a range of about 0.5 g (per day) to about 6 g (per day). In one or more embodiments, a total daily amount of the sulfonamide (e.g., sulfamethoxazole) may be in an amount in a range of about 400 mg (per day) to about 3200 mg (per day). In one or more embodiments, a total daily amount of the diaminopyridine (e.g., trimethoprim, and/or pyrimethamine) may be in an amount in a range of about 80 mg (per day) to about 500 mg (per day).

Additional representative dosing examples are provided. For example, a dosing may include a twice daily dosing provided to a subject in need, in which fosfomycin is provided in an amount of up to about or about 750 mg (each dose, 2 times/day), and in which the sulfonamide (e.g., sulfamethoxazole) is provided in an amount of up to about or about 400 mg (each dose, 2 times/day), and/or diaminopyridine (e.g., trimethoprim, and/or pyrimethamine) is provided in an amount of up to about or about 80 mg (each dose, 2 times/day). In another example, a dosing may include a thrice daily dosing provided to a subject in need, in which fosfomycin is provided in an amount of up to about or about 333 mg (each dose, 3 times/day), and in which the sulfonamide (e.g., sulfamethoxazole) is provided in an amount of up to about or about 267 mg (each dose, 3 times/day), and/or diaminopyridine (e.g., trimethoprim, and/or pyrimethamine) is provided in an amount of up to about or about 53 mg (each dose, 3 times/day). In another example, a dosing may include once daily dosing provided to a subject in need, in which fosfomycin is provided in an amount of up to about or about 4 g (one dose/day), and in which the sulfonamide (e.g., sulfamethoxazole) is provided in an amount of up to about or about 1600 mg (one dose/day), and/or diaminopyridine (e.g., trimethoprim, and/or pyrimethamine) is provided in an amount of up to about or about 250 mg (one dose/day). In a further example, a dosing may include a twice daily dosing provided to a subject in need, in which fosfomycin is provided in an amount of up to about or about 2 g (each dose, 2 times/day), and in which the sulfonamide (e.g., sulfamethoxazole) is provided in an amount of up to about or about 800 mg (each dose, 2 times/day), and/or diaminopyridine (e.g., trimethoprim, and/or pyrimethamine) is provided in an amount of up to about or about 125 mg (each dose, 2 times/day). In still another example, a dosing may include a thrice daily dosing provided to a subject in need, in which fosfomycin is provided in an amount of up to about or about 1.33 g (each dose, 3 times/day), and in which the sulfonamide (e.g., sulfamethoxazole) is provided in an amount of up to about or about 400 mg (each dose, 3 times/day), and/or diaminopyridine (e.g., trimethoprim, and/or pyrimethamine) is provided in an amount of up to about or about 75 mg (each dose, 3 times/day). In yet another example, a dosing may include a twice daily dosing provided to a subject in need, in which fosfomycin is provided in an amount of up to about or about 1.5 g (each dose, 2 times/day), and in which the sulfonamide (e.g., sulfamethoxazole) is provided in an amount of up to about or about 400 mg (each dose, 2 times/day), and/or diaminopyridine (e.g., trimethoprim, and/or pyrimethamine) is provided in an amount of up to about or about 80 mg (each dose, 2 times/day). In still another example, a dosing may include a thrice daily dosing provided to a subject in need, in which fosfomycin is provided in an amount of up to about or about 1 g (each dose, 3 times/day), and in which the sulfonamide (e.g., sulfamethoxazole) is provided in an amount of up to about or about 167 mg (each dose, 3 times/day), and/or diaminopyridine (e.g., trimethoprim, and/or pyrimethamine) is provided in an amount of up to about or about 54 mg (each dose, 3 times/day). In another example, a dosing may include once daily dosing of fosfomycin provided in an amount of up to about or about 3 g (one dose/day), and in which the sulfonamide (e.g., sulfamethoxazole) is provided twice daily in an amount of up to about or about 400 mg (two doses/day), and/or diaminopyridine (e.g., trimethoprim, and/or pyrimethamine) is provided twice daily in an amount of up to about or about 80 mg (two doses/day). In a further example, a dosing may include a thrice daily dosing provided to a subject in need, in which fosfomycin is provided in an amount of up to about or about 500 mg (each dose, 3 times/day), and in which the sulfonamide (e.g., sulfamethoxazole) is provided in an amount of up to about or about 400 mg (each dose, 3 times/day), and/or diaminopyridine (e.g., trimethoprim, and/or pyrimethamine) is provided in an amount of up to about or about 75 mg (each dose, 3 times/day). In another example, a dosing may include twice daily dosing of fosfomycin provided in an amount of up to about or about 1 g (two doses/day), and in which the sulfonamide (e.g., sulfamethoxazole) is provided twice daily in an amount of up to about or about 800 mg (two doses/day), and/or diaminopyridine (e.g., trimethoprim, and/or pyrimethamine) is provided twice daily in an amount of up to about or about 125 mg (two doses/day). Of course, additional dosing schedules are contemplated and/or suitable.

The duration of the combination (in a single formulation or when said components are provided so that there is overlapping exposure of the components) may be from five days to 10 days, or may be from 10 days to 14 days. The duration of the combination may be from 1 day and up to about 21 days, or any length therebetween, the length of time, depending in part on the severity of the infection.

The novel compositions described herein may be provided for a number of uses, including but not limited to topical, oral, and parenteral (IV) use or for inhalation. Dosage forms of the novel compositions include pharmaceutically acceptable forms that provide effective treatment against one or more bacterial infections. Said forms may include pharmaceutically acceptable salts, esters or prodrugs thereof. Said forms may further include a pharmaceutically acceptable base addition salt, which refers to those salts that retain the biological effectiveness, and properties of the free acids, which are not biologically or otherwise undesirable. These salts are prepared from addition of an inorganic base or an organic base to the free acid. Said forms may also include a pharmaceutically acceptable acid addition salt, which refers to those salts that retain the biological effectiveness, and properties of the free bases, which are not biologically or otherwise undesirable, and which are formed with inorganic acids. Said dosage forms will include dosages with acceptable side effect profiles when administered to a subject in need thereof. In one or more embodiments, the novel compositions described herein are provided as a pharmaceutical composition, which refers to a formulation containing each component of the composition along with a medium generally accepted in the art for the delivery of the novel composition on its whole or in its parts. For effective use, the pharmaceutical composition will be a biologically active composition, delivered to a subject in need thereof, such as a mammal, for example, humans. The medium will include any pharmaceutically acceptable carrier(s), diluent (s), and/or excipient(s).

In many embodiments, the novel composition will be provided at a therapeutically effective amount, which refers to that amount of the novel composition on its whole which, when administered to a subject in need thereof, is sufficient to effect treatment of a symptom, a condition, or a disease of interest in the subject or as presented by the subject. The amount of an antibiotic composition of the invention which constitutes a "therapeutically effective amount" will vary depending on the antibiotic composition, the disease or condition, and its severity, and the age of the mammal to be treated, but can be determined routinely by one of ordinary skill in the art having regard to his own knowledge, and to this disclosure. The therapeutically effective amount may be modified by pharmacokinetic, and pharmacodynamic analysis as is understood in the field. In some embodiments, the novel composition may be provided prophylactically or preventatively or protectively, which may, in some instances, be at or below a therapeutically effective amount. A representative example of pharmacokinetic parameters is provided in TABLE 13.

TABLE 13

|  | Fosfomycin | diaminopyridine (e.g., trimethoprim) | sulfonamide (e.g., sulfamethoxazole) |
| --- | --- | --- | --- |
| Dose | 3000 mg | 720 mg | 3600 mg |
| Tmax | 2 hrs | 2 hrs | 4 hrs |
| Cmax | 26.1 µg/mL | 8.5 µg/mL | 120 µg/mL |
| T½ | 5.7 hrs |  |  |
| kel (elimination rate constant) | 0.122 hrs | 0.08 hrs | 0.08 to 1 hr |
| Cmax/dose | 0.0087 mg | 0.012 mg | 0.033 mg |

Treating a subject may be treating a subject in need thereof or treating a subject preventatively or protectively. Generally, treating as described herein, and a treatment as described herein may include treatment of a symptom, or a condition, or a disease of interest, or an infection as presented by a subject, or is defending against a condition or a disease or a symptom. Treatment may include but is not limited to: (i) preventing the symptom or disease or condition from occurring in a subject (such as when such subject is predisposed to the disease or condition, and has not yet been diagnosed or is not yet symptomatic; (ii) inhibiting a symptom or disease or condition (e.g., arresting its development; (iii) relieving a symptom or disease or condition (e.g., causing regression of the symptom disease or condition; or (iv) stabilizing the symptom or disease or condition.

Embodiments described herein further include treating one or more conditions or symptoms (e.g., infections, and/or diseases associate with one or more infections caused by or considered to be associated with a microbe, including bacteria described previously). Treating may including when presenting with symptoms or prior to presenting with symptoms. Microbial infections include but are not limited to wound infections, respiratory infections, systemic infections, skin infection, sexually transmitted diseases, and related infections, gastrointestinal, urogenital infections, pneumonia, tuberculosis, gonorrhea, syphilis, sepsis, meningitis, cholera, and diarrhea associated with a microbial infection. Treating may include prophylaxis, therapy, and/or cure. Treating of a subject may involve reducing infection, preventing infection, and/or delaying or slowing the onset of an infection or an associated condition, disease, or disorder (e.g. the symptoms associated with the disease, condition, or disorder). In some embodiments, the infection may be associated with antibiotic resistant bacteria.

Formulations prepared with the described compositions may include those suitable for oral, nasal, topical (including buccal, and sublingual), intravenous, rectal, vaginal, and/or parenteral administration. The formulations may conveniently be presented in unit dosage form, and may be prepared by any methods well known in the pharmacy field. The amount of active ingredient which can be combined with additional components, and/or a carrier material to produce a single dosage form will vary depending upon the host being treated, the particular mode of administration, and other factors. The amount of active ingredient that can be combined with or without a carrier material to produce a single dosage form will, in many embodiments, generally be that amount of the compound, and/or the composition which produces a therapeutic effect. Generally, this amount will range from about 1% to about 99% of active ingredient, or from about 5% to about 80%, or any amount therein.

The described compositions may be provided as an injectable or parenteral formulation. Such compositions will include an effective amount of an excipient. The excipient will have one or more of the following functionalities: soluble; stabilization (e.g. antioxidant); anti-microbial preservation; impart tonicity (with a goal of achieving isotonicity); bulking agent. In some embodiments, the described compositions will be available in a sterile, pyrogen-free solution or as a lyophilized powder for reconstitution. They may be provided as single-use vials or formulated in, e.g., USP water for injection, or as a lyophilized powder, such as in an amount that will be reconstituted with dextrose for intravenous administration.

For oral administration, the described composition may be for immediate or sustained release (e.g., provided as granules, and/or by layering, such as a multi-layered tablet or capsule having granules therein, in which there are different release profile for each layer and/or granule, such as fast release in one layer (or set of granules), and delayed release in the other(s) which can be modulated to enable the ultimate or desired bioavailability). A binary combination may be provided into one multilayered film-coated tablet and/or capsule (as well as other suitable forms). An oral formulation may include a plurality of granules or plurality of layers or plurality of components each having its own unique release characteristics in order to maximize release and/or to ensure sufficient overlap and exposure of the components at the site of infection. A carrier may also be included for increasing AUC of one or more layers and/or set of granules, as described above. Layering, hot-melt extrusion (HME), granulation, and/or lipid drug delivery are exemplary means used to provide the described composition for oral administration. The described compositions may further comprise one or more of the following: tablet and/or capsular coating, disintegrant, surfactant, lubricant, glidant, anti-adherent, and corn starch anti-sticking agent.

Also provided are kits including one or more pharmaceutical compositions described herein. A kit may include one or more additional agents, compounds with compositions described herein. The different components of the kit may be provided in different containers. The kit may be compartmentalized to receive the containers in close confinement. The kit may also contain instructions for using the described compositions with accompanying components. Illustrative examples of containers for said kits include, but are not limited to, small glass containers, plastic containers, composite containers, or strips of plastic or paper. Containers may be those that allow a worker to efficiently transfer reagents or components from one compartment to another compartment. Such containers may also one that will accept a compound or compositions described herein, and/or may accept a resuspending solution. Said compositions being in any one or more of a powder (e.g. a lyophilized powder), precipitate, granules, tablet, gel or liquid form, as examples. Compositions described herein or one or more of the components that make us the described compositions may be provided in the same or different forms in a single kit, and may be provided in the same or different containers.

In one or more embodiments, DP, and SM may be prepared as a blend, by mixing the requisite ingredients as is known in the art. An organic solvent which is miscible with water (e.g., glycofurol or a polyethyleneglycol) may also be added during the preparation. The mixture may further comprise fosfomycin or its precursor or requisite ingredients. Alternatively, the DP, and SM may remain independent, and be prepared independently from the fosfomycin, in which case said DP, and/or the SM, and the fosfomycin may be co-administered (sequentially, or concomitantly).

Said aqueous compositions (or the DP, and/or SM and the fosfomycin independently) may be dried using known techniques, including freeze-drying, spray-drying. Precipitates may also be prepared from the aqueous compositions using methods known in the field, and dried, such as under vacuum. The resulting dry compositions, which are also a part of what is disclosed herein, may be reconverted, when desired (with or without sterilization, such as after sterilization) into solutions (e.g. injection solutions) by the addition of water or other suitable liquid for dissolving said dry components.

The compositions described herein may be used, in addition to use as injectable solutions, by other means of administration in which said combination in solution form should be used.

The compositions described herein may be used by any means of administration in which said combination in solid form should be used.

In another embodiment, the components are blended in dry form, and granulated by means known in the art (such as with a binding agent, polymeric component, etc.) to form a tablet or a pressed composition.

The compositions described herein may also be sterilized by means of known techniques which are usual in the preparation of parenteral administration forms as, for example, heat sterilization or sterile filtration.

Embodiments described herein include treating subjects infected with, and/or subjects at risk of developing, a microbial infection, including a drug-resistant microbial infection. A subject may be a mammal, including an animal or other multicellular organism. A subject may be a human. A subject may be a pet or a farm animal.

Several methods for killing the microorganisms are included with the inventions described herein. One or more methods include directly killing the microorganisms. The microorganisms may include Gram-positive bacteria. The microorganisms may include parasites. The microorganisms may include microorganisms considered resistance to alternative antimicrobial agents. The microorganisms may include microorganisms considered resistant to one or more of the ingredients used in the compositions described herein (e.g., at least one first compound or agent, and at least one second compound or agent). One or more methods may include killing the microorganisms in a subject in need thereof, the method comprising providing at least one form of the composition described herein (having at least one first compound or agent, and at least one second compound or agent). The method further comprises administering the at least one form of the composition described herein to the subject in a dose sufficient to kill or directly kill the microorganism. The method may further comprise administering the at least one form of the composition described herein to the subject in a dose and for a duration sufficient to kill or directly kill the microorganism. In addition, or as an alternative, the method may comprise administering the at least one form of the composition described herein to the subject in a dose and for a duration sufficient to control infection caused by or attributed to the microorganism. In addition, or as an alternative, the method may comprise administering the at least one form of the composition described herein to the subject in a dose and for a duration sufficient to suppress an infection caused by or attributed to the microorganism.

One or more methods described herein may include killing or inhibiting growth of microorganisms present on a surface or within an object or a subject in need thereof, the method comprising contacting the microorganisms with a formulation comprising an effective amount of one of the compositions described herein, wherein contacting results in killing or in inhibiting growth of the microorganism, the formulation comprising at least a pharmaceutically acceptable fosfomycin, and one or more of a pharmaceutically acceptable sulfonamide and/or a pharmaceutically acceptable diaminopyridine. The microorganism may be a bacteria. The microorganism may be a parasite. The microorganism may be resistant to one or more of the components that make of the formulation. The fosfomycin may be in the form of a pharmaceutically acceptable salt, ester, or prodrug, or an analog or derivative thereof, any of which have inhibitory activity in cell wall synthesis of the microorganism. The sulfonamide may be one or more sulfonamide in the form of a pharmaceutically acceptable salt, ester, or prodrug, or an analog or derivative thereof, any of which have any of which have inhibitory activity in folic acid metabolism. The diaminopyridine may be one or more diaminopyridine in the form of a pharmaceutically acceptable salt, ester, or prodrug, or an analog or derivative thereof, any of inhibit dihydrofolate reductase. The effective amount may be an amount of at least one of the fosfomycin, the diaminopyridine, and/or the sulfonamide that is less than an amount indicated as a therapeutically effective amount when used alone.

As used herein, and in the appended claims, the singular forms "a," "and," and "the" include plural referents unless the context clearly dictates otherwise. Thus, for example, reference to "an agent" or to "a composition" includes a plurality of such agents or compositions, and equivalents thereof known to those skilled in the art, and so forth. It is understood that the term "comprising" (and related terms such as "comprise" or "comprises" or "having" or "including") is not intended to exclude embodiments wherein, for example, any composition of matter, composition, method, or process, or the like, described herein may "consist of" or "consist essentially of" the described features.

Although representative processes, and articles have been described in detail herein, those skilled in the art will recognize that various substitutions and modifications may be made without departing from the scope, and spirit of what is described, and defined by the appended claims.

What is claimed includes:

1. A composition for inhibiting growth of a susceptible microorganism, or for killing the susceptible microorganism, the composition comprising:
   an effective amount of the composition, the composition being an antimicrobial, the composition comprising a combination of at least three components being provided at least as one of concomitantly or comingling, the at least three components selected as at least:
   (i) a fosfomycin, wherein the fosfomycin is an antimicrobial fosfomycin, including a salt, ester, analog, or derivative thereof, any of which will have inhibitory activity in cell wall synthesis of the susceptible microorganism;
   (ii) a sulfonamide, wherein the sulfonamide is an antimicrobial sulfonamide, including a salt, ester, analog, or derivative thereof, any of which will have inhibitory activity in folic acid metabolism of the susceptible microorganism; and
   (iii) a diaminopyridine, wherein the diaminopyridine is an antimicrobial diaminopyridine, including a salt, ester, analog, or derivative thereof, any of which will inhibit dihydrofolate reductase of the susceptible microorganism, the composition being in a pharmaceutically acceptable form, and in the effective amount, the combination of the at least three components displaying synergistic activity against the susceptible microorganism, thereby inhibiting growth of the susceptible microorganism, or killing the susceptible microorganism, wherein the effective amount is a ratio of the fosfomycin to the diaminopyridine to the sulfonamide that is between about 0.95:0.013:0.039, respectively, and 1.05:0.057:0.342, respectively.

2. The composition of claim 1, wherein the synergistic activity is against Gram-positive bacteria, and Gram-negative bacteria.

3. The composition of claim 1, wherein the composition further comprises an excipient.

4. The composition of claim 1, wherein the sulfonamide to the diaminopyridine is in a ratio of between about 3:1 and 6:1.

5. The composition of claim 1, wherein the composition is at least one of: (i) formulated for administration to a subject in need thereof; and (ii) formulated for administration to a subject in need thereof, in which the subject is further supplemented with another agent selected from at least one of the group consisting of antibiotic, antiviral agent, antifungal agent, anti-parasitic agent, and combinations thereof.

6. The composition of claim 1, wherein the composition further comprises a carrier selected in an amount such that the carrier in the selected amount increases an area under a plasma concentration-time curve (AUC) over a mean inhibitory concentration (MIC) of at least one of the at least three components of the composition after administration of the effective amount of the composition to a subject in need thereof, the increase being measurable and determined when compared with an AUC over MIC after administration of an effective amount of the composition without the carrier, wherein the carrier is a linear chain polysaccharide selected from at least one or more of cellulose, microcrystalline cellulose, hydroxymethyl cellulose, hydroxypropylcellulose, and polyvinylpyrrolidone.

7. The composition of claim 1, wherein at least one of the at least three components of the composition is in an amount such that the at least one of the at least three components exhibits an increase in an area under a plasma concentration-time curve (AUC) over a mean inhibitory concentration (MIC) of the at least one of the at least three components of the composition after administration of the effective amount of the composition to a subject in need thereof, the increase determined when compared with an AUC over MIC of the at least one of the at least three components of the composition when administered alone and at its effective amount.

8. The composition of claim 1, wherein the susceptible microorganism is clinically resistant to at least one of the at least three components when the at least one of the at least three components is used alone against the clinically resistant susceptible microorganism.

9. The composition of claim 1, wherein the susceptible microorganism is at least one of a bacteria selected from at least one of *Staphylococcus* spp., including methicillin-resistant *Staphylococcus aureus*, *Streptococcus* spp., *Enterococcus* spp., *Bacillus anthracis*, Enterobacteriaceae, *Escherichia coli*, *Klebsiella pneumoniae*, *Enterobacter cloacae*, *Pseudomonas aeruginosa*, *Stenotrophomonas maltophila*, *Burkholderia* spp., *Acinetobacter baumanii*, *Proteus mirabilis*, *Proteus vulgaris*, *Providencia* sp., *Morganella morganii*, *Haemophilus influenzae*, *Moraxella catarrhalis*, *Legionella pneumophila*, and *Yersinia pestis*, and the composition is formulated to be effective at killing or inhibiting growth of the at least one of the bacteria.

10. The composition of claim 1, wherein the effective amount of the composition includes an amount of at least one of the at least three components that is less than an amount of that component indicated as a therapeutically effective amount when used alone.

11. An antibiotic pharmaceutical composition comprising in a formulation at least:

a fosfomycin; and at least one of a sulfonamide and a diaminopyridine, wherein the at least one of the sulfonamide and the diaminopyridine is an at least one of an antimicrobial sulfonamide and an antimicrobial diaminopyridine, including a pharmaceutically acceptable salt, or ester, thereof, the antibiotic pharmaceutical composition inhibiting growth of a susceptible microorganism, or killing the susceptible microorganism, the susceptible microorganism suspected of causing an infection in a subject, wherein the fosfomycin is an antimicrobial fosfomycin and is provided in a pharmaceutically acceptable form, including a salt, or ester, thereof, any of which will have inhibitory activity on cell wall synthesis of the susceptible microorganism, and wherein the antibiotic pharmaceutical composition, comprising a combination of the fosfomycin and at least one of the sulfonamide and the diaminopyridine, has at least an effective amount of the fosfomycin and at least one of the sulfonamide and the diaminopyridine to be synergistic in activity against the susceptible microorganism, thereby inhibiting growth of the susceptible microorganism, or killing the susceptible microorganism, wherein, for the subject, a minimum daily amount of the fosfomycin is at or about 3000 mg, a minimum daily amount of the sulfonamide is 400 mg, and a minimum daily amount of the diaminopyridine is 80 mg.

12. The antibiotic pharmaceutical composition of claim 11, wherein with the antibiotic pharmaceutical composition there is any one or more of the following:

(i) a mean inhibitory concentration of the composition when provided for inhibiting growth of the susceptible microorganism is below a resistance breakpoint identified for each of the fosfomycin and the at least one of the sulfonamide and the diaminopyridine, when individually and independently provided for inhibiting growth of the susceptible microorganism in vitro, the resistance breakpoint having been identified by at least one of the Clinical Laboratories Standards Institute, and the European Committee on Antimicrobial Susceptibility Testing, and is at least four fold below an inhibitory concentration for at least one of the fosfomycin and the at least one of the sulfonamide and the diaminopyridine, individually; and (ii) an amount of one or more of the fosfomycin, and the at least one of the sulfonamide and the diaminopyridine, in the antibiotic pharmaceutical composition, is less than an amount indicated as a therapeutically effective amount when the one or more of the fosfomycin, and the at least one of the sulfonamide and the diaminopyridine, is used alone.

13. The antibiotic pharmaceutical composition of claim 11, wherein the sulfonamide in the formulation is in a pharmaceutically acceptable form and is selected from at least one of an esterified sulfonamide that will exhibit inhibitory activity in synthesis of dihydrofolate in the susceptible microorganism, a sulfonamide salt that will exhibit inhibitory activity in synthesis of folic acid in the susceptible microorganism, an analog thereof that will exhibit inhibitory activity in synthesis of dihydrofolate in the susceptible microorganism, a derivative thereof that will exhibit inhibitory activity in synthesis of dihydrofolate in the susceptible microorganism, and sulfamethoxazole.

14. The antibiotic pharmaceutical composition of claim 11, wherein the diaminopyridine in the formulation is in a pharmaceutically acceptable form and is selected from at least one of an esterified diaminopyridine that will inhibit dihydrofolate reductase in the susceptible microorganism, a diaminopyridine salt that will inhibit dihydrofolate reductase in the susceptible microorganism, an analog thereof that will inhibit dihydrofolate reductase in the susceptible microorganism, a derivative thereof that will inhibit dihydrofolate reductase in the susceptible microorganism, trimethoprim, pyrimethamine, and iclaprim.

15. The antibiotic pharmaceutical composition of claim 11, wherein the susceptible microorganism is one or more of: (i) one suspected to cause a bacterial infection selected from the group consisting of a gastrointestinal infection, genitourinary infection, respiratory infection, skin infection, systemic infection, wound infection, and sexually transmitted infection; and (ii) considered resistant to any one or more of the fosfomycin, the sulfonamide, and the diaminopyridine.

16. The antibiotic pharmaceutical composition of claim 11, wherein the susceptible microorganism resides in or on the subject, and the antibiotic pharmaceutical composition in the formulation is formulated for administration in a therapeutically effective amount to the subject.

17. The antibiotic pharmaceutical composition of claim 11, wherein the antibiotic pharmaceutical composition in the formulation is formulated for administration in a therapeutically effective amount, and the therapeutically effective amount is a therapeutically effective amount of the fosfomycin, and a therapeutically effective amount of one or both of the at least one of the sulfonamide and the diaminopyridine.

18. The antibiotic pharmaceutical composition of claim 11 further comprising an excipient.

19. The antibiotic pharmaceutical composition of claim 11, wherein the susceptible microorganism is at least one of a bacteria selected from at least one of *Staphylococcus* spp., including methicillin-resistant *Staphylococcus aureus*, *Streptococcus* spp., *Enterococcus* spp., *Bacillus anthracis*, Enterobacteriaceae, *Escherichia coli*, *Klebsiella pneumoniae*, *Enterobacter cloacae*, *Pseudomonas aeruginosa*, *Stenotrophomonas maltophila*, *Burkholderia* spp., *Acinetobacter baumanii*, *Proteus mirabilis*, *Proteus vulgaris*, *Providencia* sp., *Morganella morganii*, *Haemophilus influenzae*, *Moraxella catarrhalis*, *Legionella pneumophila*, and *Yersinia pestis*, and the composition is formulated to be effective at killing or inhibiting growth of the at least one of the bacteria.

20. The antibiotic pharmaceutical composition of claim 11, wherein in the formulation, the antibiotic pharmaceutical composition comprises both the sulfonamide and the diaminopyridine, and the sulfonamide and the diaminopyridine are in a ratio of between about 3:1 and 6:1, respectively.

21. The antibiotic pharmaceutical composition of claim 11, wherein the subject is any of a human, and an animal.

* * * * *